US007825154B2

(12) United States Patent
Bavari et al.

(10) Patent No.: US 7,825,154 B2
(45) Date of Patent: Nov. 2, 2010

(54) SMALL MOLECULE INHIBITORS OF BOTULINUM NEUROTOXINS

(75) Inventors: Sina Bavari, Frederick, MD (US); Rick Gussio, Frederick, MD (US); James C. Burnett, Richmond, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1069 days.

(21) Appl. No.: 11/464,007

(22) Filed: Aug. 11, 2006

(65) Prior Publication Data

US 2007/0112049 A1    May 17, 2007

Related U.S. Application Data

(60) Provisional application No. 60/707,531, filed on Aug. 12, 2005, provisional application No. 60/723,442, filed on Oct. 5, 2005.

(51) Int. Cl.
*A61K 31/40* (2006.01)
*A01N 43/38* (2006.01)
*A01N 43/06* (2006.01)
*A01N 43/08* (2006.01)
*C07D 333/02* (2006.01)

(52) U.S. Cl. .................. 514/411; 514/438; 514/461; 549/29

(58) Field of Classification Search ........... 514/411, 514/438, 461; 549/29
See application file for complete search history.

(56) References Cited

U.S. PATENT DOCUMENTS

2005/0251345 A1* 11/2005 Bavari et al. ................ 702/19

OTHER PUBLICATIONS

Weidner-Wells et al. "Amidono Benimidazole Inhibitors of Bacerial Two-Component Systems" Bioorganic & Medicinal Chemistry Letters, 2001, vol. 11, pp. 1545-1548.*
Mota-Meira et al. "MICs of Mutacin B-Ny266, Nisin A, Vancomycin, and Oxacillin against Bacterial Pathogens" Antimicrobial abents and chemotherapy, Jan. 2000, pp. 24-29.*
Anne, J. et al. (1980) "Antifungal and Antibacterial Activities of Diarylamidine Derivatives" Antimicrobial Agents & Chemotherapy 18(2):231-239.
De. Clercq et al. (1980) "Diaryl Amidine Derivatives as Oncornaviral DNA Polymerase Inhibitors" J. Med. Chem. 23:787-795.
Tidwell et al. (1978) "Diarylamidine Derivatives with One or Both of the Aryl Moieties Consisting of an Indole or Indole-like Ring, Inhibitors of Arginine-Specific Esteroproteases" J. Med. Chem. 21(7):613-623.

* cited by examiner

*Primary Examiner*—Sreeni Padmanabhan
*Assistant Examiner*—Kendra D Carter
(74) *Attorney, Agent, or Firm*—Elizabeth Arwine

(57) ABSTRACT

Disclosed herein are methods of inhibiting the activity of Botulinum neurotoxin A metalloprotease with the compounds disclosed herein. Also disclosed are methods of treating, inhibiting or preventing intoxication caused by bacteria of at least one bacterial strain in a subject, and pharmaceutical and cosmetic compositions comprising the compounds disclosed herein.

13 Claims, 3 Drawing Sheets

| NSC | $K_i$ | Query Fit | Distances (Å) | | | |
|---|---|---|---|---|---|---|
| | | | $A-B^1$ | $A-C^1$ | $A-F^1$ | $Total^2$ |
| 341909 | 3.0μM | | 7.5 | 4.8 | 13.5 | 19.6 |
| 308574 | 6.0μM | | 12.8 | 3.9 | 16.6 | 19.9 |
| 240898 | 10.0μM | | 9.6 | 3.9 | 11.9 | 17.8 |
| 341907 | 10.0μM | | 8.8 | 4.5 | 12.8 | 19.3 |

1. Distance taken from plane centroids
2. Total length of the compound

Figure 1

SMALL MOLECULE INHIBITORS OF BOTULINUM NEUROTOXINS

CROSS-REFERENCE TO RELATED APPLICATIONS

This application claims the benefit of U.S. Provisional Patent Application Ser. Nos. 60/707,531, filed 12 Aug. 2005, and 60/723,442, filed 5 Oct. 2005, both of which are herein incorporated by reference in their entirety.

ACKNOWLEDGEMENT OF GOVERNMENT SUPPORT

This invention was made by employees of the United States Army Medical Research and Materiel Command, which is an agency of the United States Government. The Government has certain rights in this invention.

BACKGROUND OF THE INVENTION

1. Field of the Invention

The present invention relates to compounds which inhibit botulinum neurotoxin. In particular, the present invention relates to compounds which inhibit botulinum neurotoxin serotype A light chain (BoNT/A LC) metalloprotease activity.

2. Description of the Related Art

Botulinum neurotoxins (BoNTs) are produced by spore forming anaerobic bacteria *Clostridium botulinum*, and are among the most lethal of biological poisons ($LD_{50}$=0.001 µg per Kg). See Schmidt & Stafford (2003) Appl. Environ. Microbiol. 69:297-303; Kessler & Benecke (1997) Neurotoxicology 18:761-770; and Burnett et al. (2005) Nat Rev Drug Discov 4(4):281-297. Seven immunologically distinct BoNT serotypes (designated A-G) have been identified. See Simpson, L. L. (1989) BOTULINUM NEUROTOXIN AND TETANUS TOXIN, Academic Press, New York.

Exposure to BoNTs, for example, through contaminated food, can result in life threatening flaccid paralysis. See Shapiro, et al. (1998) Ann. Intern. Med. 129:221-228. Furthermore, BoNTs have been weaponized in highly toxic aerosol form, and consequently pose a significant threat to both to civilian and military populations. See Franz, et al. (1997) JAMA 278:399-411; and Amon, et al. (2001) JAMA 285: 1059-1070.

As indicated, these enzymes have been weaponized in aerosol medium, and airborne release or direct contamination (e.g. foodstuffs) represent significant threats to both military and civilian populations. See Paddle, B M (2003) J Appl Toxicol 23(3):139-170; Clarke, S C (2005) Br J Biomed Sci 62(1):40-46; Hicks et al. (2005) Curr Med Chem 12(6):667-690; and Josko, D (2004) Clin Lab Sci 17(1):30-34. And, with the increased use of BoNTs as therapies for a range of medical conditions and superficial cosmetic purposes, there is the increased potential for accidental overdosing. Furthermore, as the popularity of BoNTs as therapeutics continues to grow, these enzymes are increasingly being manufactures overseas, where less strict controls may allow clandestine organizations to obtain large quantities of these toxins in very concentrated, pure, and easily stored formulations. See Comella & Pullman (2004) Muscle Nerve 29(5):628-644; Gormley et al. (1997) Muscle Nerve Suppl 6:S14-20; Marks, J D (2004) Anesthesiol Clin North America 22(3):509-532, vii; Noonan & Adler (2002) Newsweek 139(19):50-56, 58; O'Brien, C F (2001) Adv Neurol 87:265-269; O'Brien, C F (2002) Clin J Pain 18(6 Suppl):S182-190; O'Brien, D (2003) J Perianesth Nurs 18(2):126-134; Rossetto (2001) Toxicon 39(1):27-41; Shukla & Sharma (2005) Crit Rev Microbiol 31(1):11-18; and Turton et al. (2002) Trends Biochem Sci 27(11):552-558. As a result, there is an urgent need for therapeutic countermeasures against BoNTs. See Goodnough, et al. (2002) FEBS Lett. 513:163-168.

BoNT is secreted as a holotoxin composed of two peptide chains that are linked by a disulfide bridge. See Lacy & Stevens (1999) J. Mol. Biol. 291:1091-1104. The heavy chain is responsible for: (1) targeting and binding to surface receptors on nerve terminals; (2) translocation into the neuronal cytosol via the formation of a low pH endosome; and (3) protecting the substrate binding cleft of the light chain prior to neuronal internalization. See Turton, et al. (2002) Trends Biochem. Sci. 27:552-558; and Singh, B. R. (2000) Nat. Struct. Biol. 7 (2000) 617-619. The light chain, which dissociates from the heavy chain in the low endosomal pH, is released into the cytosol where it acts as a zinc metalloprotease that cleaves soluble NSF-attachment protein receptor (SNARE) proteins: synaptosomal-associated protein of 25 kDa (SNAP-25), synaptobrevin, and syntaxin. BoNT serotypes A, C, and E cleave SNAP-25; serotypes B, D, F, and G cleave synaptobrevin; and serotype C can also use syntaxin as substrate. See Binz, et al. (1994) J. Biol. Chem. 269:1617-1620; Schiavo, et al. (1992) Nature 359:832-835; Schiavo, et al. (1993a) J. Biol. Chem. 268:23784-23787; Schiavo, et al. (1993c) J. Biol. Chem. 268:11516-1151915; Schiavo, et al. (1993b) J. Biol. Chem. 269:20213-20216; and Blasi, et al. (1993b) EMBO J. 12:4821-4828. Without functional SNARE complexes, acetylcholine is not released into neuromuscular junctions, thereby leading to paralysis.

Research to identify peptide and small molecule inhibitors of BoNT serotype A (BoNT/A) has targeted both holotoxin translocation and light chain (BoNT/A LC) metalloprotease activity. Sheridan et al. and Deshpande et al. have shown that a number of antimalarial agents interfere with BoNT/A translocation into nerve cytoplasm. See Sheridan, et al. (1997) Toxicon 35:1439-1451; and Deshpande, et al. (1997) Toxicon 35:433-445.

Specifically, it has been shown that several antimalarial compounds act subsequent to toxin binding to cell-surface receptors, and it has been hypothesized that these agents inhibit BoNT/A cytosol entry by raising endosomal pH (an endosomal pH of 5.5 or lower is needed for release into the cytoplasm). Hayden et al. have found that BoNT/A LC is inhibited by mM concentrations of known protease inhibitors: captopril, lysinopril, and enalapril. See Hayden, et al. (2003) J. Appl. Toxicol. 23:1-7. In the same study, it was also reported that a number of short peptides, from specific "hinge" libraries, inhibit BoNT/A LC activity by as much as 51% at concentrations as low as 0.5 µM. Using a chromatographic method, Schmidt et al. identified the peptide motif CRATKML as a potent inhibitor. See Schmidt, et al. (1998) FEBS Lett. 435:61-64. In a subsequent study, the Cys residue of CRATKML was replaced with thiol containing organic moieties, and it was found that a 2-mercapto-3-phenylpropionly containing derivative was the most effective (Ki=0.3 µM). See Schmidt & Stafford (2002) FEBS Lett. 532:423-426.

Neither the currently available BoNT antitoxin nor antibodies can counter these toxins once they are inside neurons; currently, critical care mechanical ventilation is the only treatment option. However, the effects of internalized BoNTs can last for months, and mechanical ventilation would be impractical if even a limited number of individuals were simultaneously intoxinated. See Meunier et al. (2003) Mol Cell Neurosci 22(4):454-466; and Eleopra et al. (1998) Neurosci Lett 256(3): 135-138. Furthermore, antitoxin administration would preclude vaccinated individuals from any form of highly beneficial BoNT medical therapy.

Thus, a need exists for small molecule (non-peptidic) inhibitors of BoNT/A LC metalloprotease activity.

SUMMARY OF THE INVENTION

The present invention generally relates to compounds that inhibit BoNT/A LC metalloprotease activity.

In some embodiments, the present invention provides a method of inhibiting the activity of the Botulinum neurotoxin A metalloprotease which comprises contacting Botulinum neurotoxin A metalloprotease with at least one compound having the following structural formula:

where Y is wherein
n is 1 or 2;
$X^1$, $X^2$, $X^3$, $X^4$, $X^5$ and $X^6$ are each independently N, S, O, $SO_2$, $CR^7$ or $NR^8$ and at least one of $X^1$ or $X^2$ is N, S, O, $SO_2$, or $NR^8$;
L is a linker which may be a direct bond or where Z is an optionally substituted alkyl, alkenyl, dialkenyl, trialkenyl, or aryl, or C(O)NH; and
$R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate; and
$R^8$ is hydrogen, OH, a halogen, or an optionally substituted alkyl.

In some embodiments, at least one of $R^1$, $R^2$, $R^3$, or $R^4$ is hydrogen, amidine, 2-imidazoline, amino, guanidine, methyl, aminomethyl-hydroxamine, or methylamine-guanidine. In some embodiments, $R^5$ is hydrogen, amidine, 2-imidazoline, amino, guanidine, methyl, aminomethyl-hydrox- amine, methylamine-guanidine, 4-oxy-benzamidine, 1H-indole-6-caboxamidine, or 1H-indole-5-carboxamidine. In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole. In some embodiments, at least one of $X^1$ or $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine). In some embodiments, at least one of $X^3$, $X^4$, $X^5$, or $X^6$ is N, NH, S, O, $SO_2$, or CH. In some embodiments, at least one of $R^1$, $R^2$, $R^3$, $R^4$, $R^5$, $R^6$, or $R^7$ is —H, —$CH_3$, —$NH_2$, In some embodiments, $R^5$ is —$NH_2$, In some embodiments, $R^6$ is In some embodiments, $R^7$ is —H, —CH$_3$, —NH$_2$,

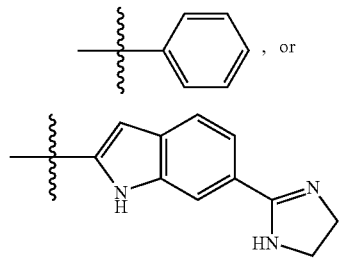

In some embodiments, $R^8$ is —H, —(CH$_2$)$_2$OH, or —(CH$_2$)$_2$Cl. In some embodiments, L is a direct bond,

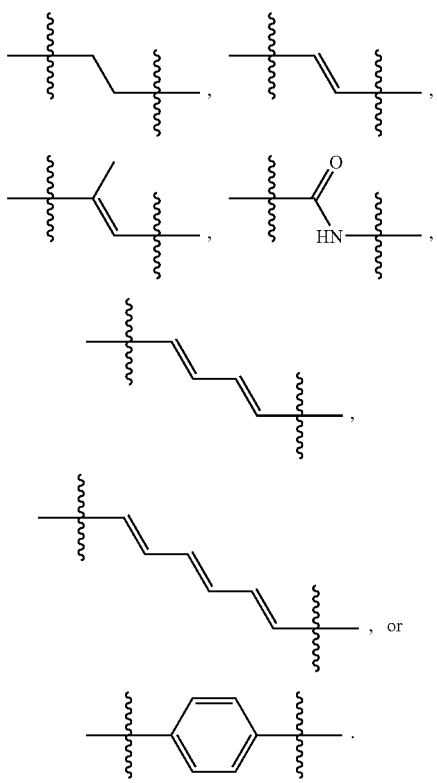

In some embodiments, the compound has the following structural formulae:

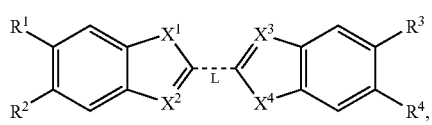

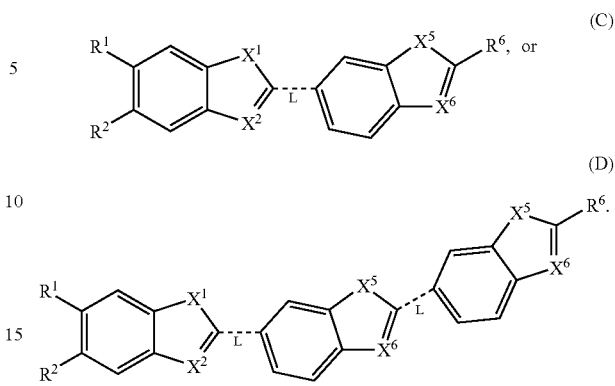

In some embodiments, the compound is NSC 92833, NSC 103699, NSC 103701, NSC 130681, NSC 240890, NSC 240891, NSC 240893, NSC 240894, NSC 240895, NSC 240896, NSC 240897, NSC 240898, NSC 240899, NSC 240900, NSC 266472, NSC 266474, NSC 266475, NSC 266476, NSC 266477, NSC 266482, NSC 278995, NSC 278996, NSC 278997, NSC 278999, NSC 290107, NSC 290108, NSC 290109, NSC 290111, NSC 291103, NSC 294199, NSC 294200, NSC 294201, NSC 294202, NSC 294203, NSC 294204, NSC 294206, NSC 294207, NSC 294208, NSC 294494, NSC 300509, NSC 300510, NSC 300511, NSC 300512, NSC 302569, NSC 308569, NSC 308570, NSC 308571, NSC 308572, NSC 308573, NSC 308574, NSC 317880, NSC 317881, NSC 317883, NSC 317884, NSC 317885, NSC 317886, NSC 317887, NSC 328398, NSC 330687, NSC 330688, NSC 330689, NSC 330690, NSC 341082, NSC 341907, NSC 341909, NSC 341910, NSC 341911, NSC 352341, NSC 369718, NSC 369721, NSC 607617, or NSC 12155. In some embodiments, the compound is NSC 341909, NSC 308574, NSC 240898, NSC 341907, NSC 266472, NSC 330690, NSC 278999, NSC 308571, NSC 290107, NSC 290108, NSC 294200, NSC 317884, NSC 317884, NSC 294203, NSC 294494, NSC 317881, NSC 330688, NSC 317886, NSC 317833, NSC 328398 NSC 352341, NSC 294204, NSC 341911, NSC 300511, NSC 607617, NSC 294202, NSC 317880, NSC 240899, NSC 294201, NSC 291103, NSC 308573, NSC 290109, NSC 294206, NSC 308570, NSC 294199, NSC 369723, or NSC 300510.

In some embodiments, the present invention provides a compound having the following structural formula:

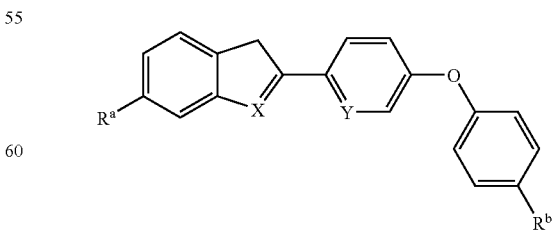

wherein $R^a$ and $R^b$ are each independently —CN, —CONH$_2$, or —C(=NH)NH$_2$; X is —NH or O; and Y is N or —CH,

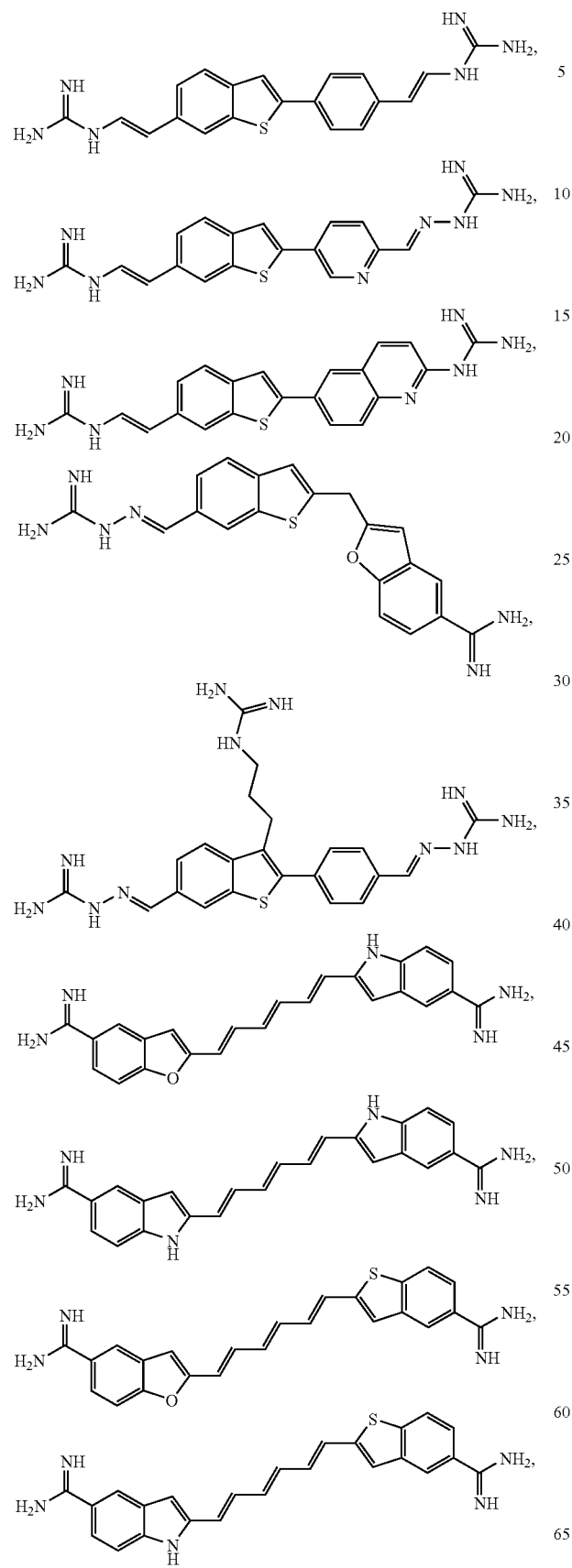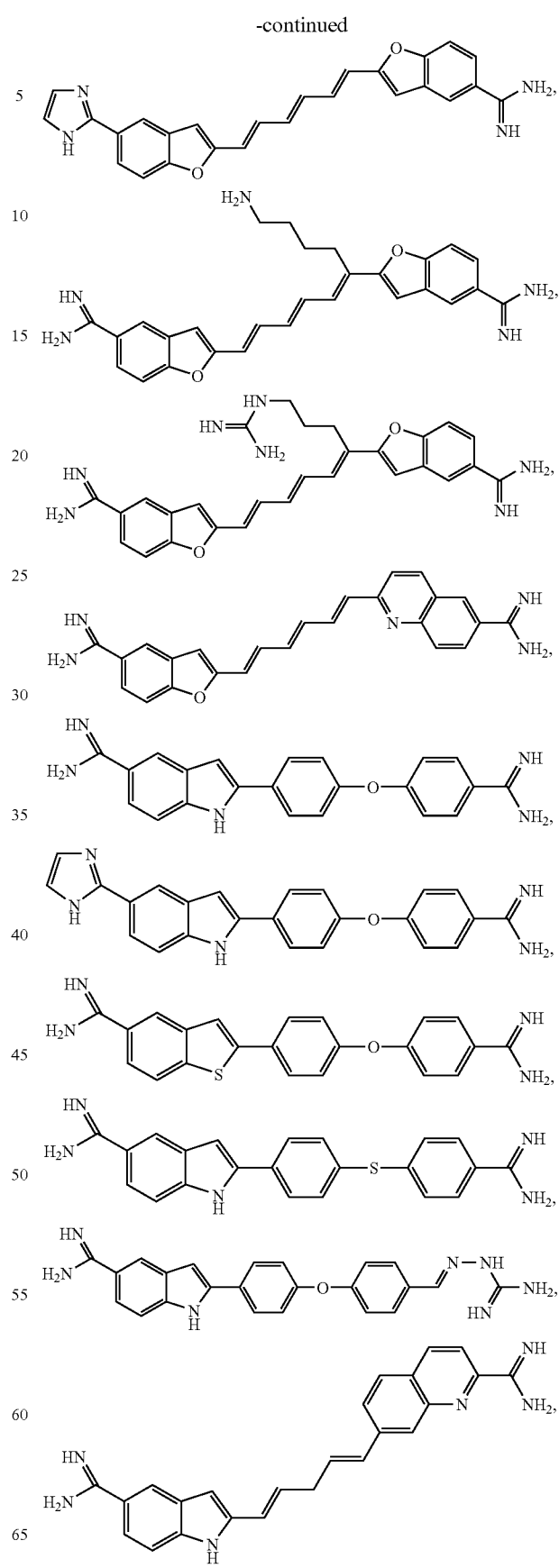

In some embodiments, the present invention provides a method of inhibiting the activity of Botulinum neurotoxin A metalloprotease which comprises contacting Botulinum neurotoxin A metalloprotease with at least one compound provided herein.

In some embodiments, the present invention provides a method of treating, inhibiting or preventing a subject from being intoxicated by Botulinum toxin which comprises administering to the subject a therapeutically effective amount of at least one compound provided herein.

In some embodiments, the present invention provides a pharmaceutical composition comprising at least one compound provided herein and a pharmaceutically acceptable carrier.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 is a table which exemplifies some compounds of the present invention, their $K_i$ values and pharacophore query fits and distances between pharmacophore components.

FIG. 3A shows raw data obtained for 30 injections of 10 μl of 1.3 mM NSC 240848 solution into the sample cell containing 50 μM BoNT/A LC (after substraction of the integration baseline).

FIG. 3B shows normalized integrated enthalpies plotted against the molar ratio NSC 240898:BoNT/A LC. The solid line corresponds to the best fit curve obtained by non-linear least square fit minimization. The binding followed a 1:1 stoichiometry and is largely entropy-driven. Due to the low affinity of the interaction, a large excess of the inhibitor was necessary to drive the titration to saturation. Protein concentration was determined by amino acid analysis (Molecular Structure Facility, Univ. Calif. Davis), and NSC 240898 concentration was confirmed by UV/Vis absorbance measurements.

DETAILED DESCRIPTION OF THE INVENTION

Figure 2A:
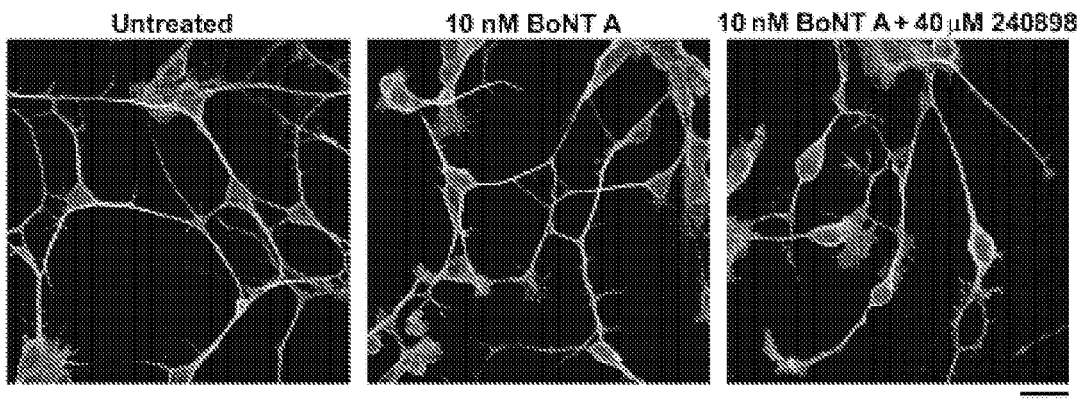
FIG. 2A shows that NSC 240898 lacks substantial cytotoxic effects on chick spinal motor neurons at concentrations up to about 40 μM. Staining for tubulin (green), actin filaments (red), and DNA (blue) show no gross morphological abnormalities in neurons after 3.5 hours incubation with either 10 nM BoNT/A holotoxin or inhibitor+10 nM BoNT/A holotoxin when compared to untreated neurons. Scale bar=20 μm.

The pharmacophore model for BoNT/A LC metalloprotease inhibition provided in U.S. Patent Publication No. 20050153945, which is herein incorporated by reference, was used to screen for small molecule compound candidates that would likely inhibit BoNT/A LC metalloprotease activity. As disclosed herein, several imidazoline compounds were identified and found to inhibit BoNT/A LC metalloprotease activity.

Identification of Candidate Small Molecule Inhibitors

Candidate small molecule inhibitors of BoNT/A LC metalloprotease activity were identified by pharmacophore analysis, molecular dynamic and molecular docketing studies.

1. Initial BoNT/A LC Pharmacophore

Previously, Burnett et al. identified a diverse range of compounds that inhibit the metalloprotease activity of the BoNT/A LC. See U.S. Patent Publication No. US 20050153945 and Burnett et al. (2003) Biochem. Biophys. Res. Commun. 310 (1):84-93, which are herein incorporated by reference. A high-throughput fluorescence-based assay was initially used to screen the NCI diversity set, a collection of 1990 molecules that were selected to cover a wide range of conformational space, and at the same time provide pharmacophore diversity and structural rigidity. Then a HPLC-based assay known in the art was used to eliminate false positives. See Schmidt et al. (2003) Appl Environ Microbiol 69:297-303, which is herein incorporated by reference. The resulting set of inhibitors, which were tested at 20 μM concentrations, in the presence of 0.1 mM substrate, comprised 21 structurally diverse compounds with potencies ranging from about 14% to about 100% inhibition of BoNT/A LC metalloprotease activity. The compounds possessing greater than about 40% inhibition were NSC 625324 (silver sulfadiazine), NSC 661755 (Michellamine B), NSC 357756, NSC 119889, NSC 86372, NSC 130796 and NSC 402959.

Congeneric series of N,N-bis(7-chloroquinolin-4yl)alkanediamines and N,N-bis(7-chloroquinolin-4yl)heteroalkanediamines (collectively referred to as bisquinolines or BQs) were also examined for BoNT/A LC inhibition. See Vennerstrom et al. (1992) J Med Chem 35:2129-2134; and Vennerstrom et al. (1998) J Med Chem 41:4360-4364, which are herein incorporated by reference. These compounds were found to be non-zinc chelators. Five readily available antimalarial drugs—amodiaquine, chloroquine, quinacrine, quinidine, and quinine—were also tested, as they share similar structural features with the BQs. The antimalarial drugs that were found to inhibit BoNT/A LC protease activity in our study have previously been shown to increase the time to BoNT/A holotoxin induced muscle paralysis by interfering with toxin translocation into the nerve cytoplasm. See Deshpande et al. (1997) Toxicon 35:433-445; and Sheridan et al. (1997) Toxicon 35:1439-1451, which are herein incorporated by reference. Thus, as provided herein, the compounds of the present invention may be used to inhibit both BoNT/A entry into the cytoplasm and protease activity of the LC.

2. BoNT/A LC Molecular Dynamics

X-ray crystal structures of BoNT/A have been solved; however, they leave an information gap with regard to the periodic motion of the LC. In particular, conformational changes in and around the substrate binding cleft could have profound effects on the design of inhibitors. Consequently, a molecular dynamics study was conducted to explore the motion of the BoNT/A LC over time. See Burnett et al. (2005) Bioorg Med Chem 13:333-341, which is herein incorporated by reference. Results from these analyses indicated that LC α-helices and β-sheets remain relatively unchanged over the course of a 1 ns dynamics trajectory. However, significant conformational flexibility in surface loops bordering the substrate binding cleft was observed. Extensive analyses indicated that these loops might possess the ability to partially shield the substrate binding cleft from the solvent front. Based on molecular docking studies with identified inhibitors, the observed reorientation of these loops toward the enzyme's substrate binding cleft may serve to provide additional residue:inhibitor (or substrate) contacts, and facilitate inhibitor desolvation. This information was used to refine the pharmacophore for BoNT/A LC inhibition.

3. Molecular Docking of mpp-RATKML.

To improve the structure-based understanding of BoNT/A LC, the binding mode for a potent inhibitor, 2-mercapto-3-phenylpropionyl-RATKML (SEQ ID NO:1) (mpp-RATKML, $K_i$=330 nM), was studied in order to reveal steric space and residue contacts not ascertained by the original pharmacophore model and molecular dynamic studies.

To ensure that we generated the most realistic model possible, we adopted a number of strict molecular docking criteria: (1) the inhibitor's sulfur (S), which coordinates the enzyme's catalytic Zinc (Zn), must do so with a distance and incidence angle consistent with available data from the Cambridge Structural Database (CSD) and the Protein Data Bank (PDB); (2) the binding mode must adhere to the hydrophobicity-first rule of molecular docking; 3) the inhibitor's intermolecular non-bonded contacts and its intramolecular conformation must be hydropathically and structurally feasible; and 4) the binding mode of the inhibitor must rationalize its structure activity relationship (SAR). See Schmidt & Stafford (2002) FEBS Lett 532:423-426; Schmidt et al. (1998) FEBS Lett 435:61-64; Alberts et al. (1998) Protein Sci. 7:1700-1716; and Roe et al. (1999) J. Mol. Model. 5:134-140, which are herein incorporated by reference.

An acceptable binding mode for the pseudo-peptide using an energy refined X-ray crystal structure of the BoNT/A LC possessing the highest resolution (PDB 1E1H, resolution=1.8 Å) was not readily identified. When, however, an enzyme conformer from a previous dynamics trajectory of 1E1H was used, a biochemically feasible binding mode was obtained. In brief, for the mpp portion of the inhibitor, the phenyl substituent engaged in face-to-face π stacking with the side chain phenyl of Phe 193 (in addition to maintaining favorable hydrophobic contacts with the Phe 162 and Thr 219 side chains). Furthermore, the S—Zn interaction was maintained within a specified distance and an angle of incidence that were verified by examining numerous structures form the CSD and PDB. The side chain methylenes of the inhibitors Arg packed with good hydrophobic—hydrophobic complementarity in the hydrophobic pocket created by loop 1 (residues 48-78) reorientation during the dynamics simulation. Desolvation of the hydrophobic portion of the Arg side chain dictated the position of its cationic guanidinium, which engaged in hydrogen bonds with the side chain carboxylates of residues Glu 63 (of loop 1) and Glu 163 (of the polar contact region).

The inhibitor's Ala, Thr, Lys, Met and Leu residues were systematically docked and optimized in the substrate binding cleft using the same strict docking criteria indicated above. The Ala residue is buried in the substrate binding cleft, resting behind the side chain imidazole of His 226, near the side chain methylene of Cys 164, and away from the side chain carboxylate of Glu 261. The amphipathic Thr side chain is positioned so that its methyl substituent points toward the substrate binding cleft and engages in favorable hydrophobic contacts with the Val 67 side chain, while its polar hydroxyl moiety is oriented toward the solvent. The side chain methylenes of the inhibitor's Lys residue desolvate by lining up parallel to the side-chain methylenes of Lys 165—this positions the residue's cationic Nζ within hydrogen bonding distance to both the side chain carboxylate of Glu 54 and the side chain amide carbonyl oxygen of Asn 52 (both of these residues are brought into closer association with the BoNT/A LC substrate binding cleft via loop 1 reorientation). The Met side chain sulfur atom engages in a weak, favorable contact with the side chain guanidinium of Arg 230, while its Cε atom packs against the P238 pyrrolidine. Finally, the side chain of the inhibitor Leu sits slightly above the backbone of loop 2 (residues 167-180), which is the steric boundary at this end of the substrate binding cleft. The hydrophobic Leu side chain is accommodated by weak, but favorable hydrophobic contacts with the side chain of V171, while the carbonyl oxygen of the amide bond between the inhibitor Met and Leu residues engages in a weak hydrogen bond with the backbone amide nitrogen of V171. The terminal amide of the inhibitor faces the solvent. The docked model of mpp-RATKML was found to be highly desolvated.

4. Designing More Potent Small Molecule Inhibitors

Pharmacophore components were mapped to the docked conformation of mpp-RATKML and it was found that the pseudo-peptide and small molecule inhibitors share common structural/functional group features that confer binding. Thus, incorporating features from the pseudo-peptide binding mode may enhance the potencies of small molecule inhibitors.

For example, the mpp phenyl substituent, is a sterically and hydropathically superior match for binding subsite 1 compared to smaller hydrophobic moieties (i.e., chloro, methyl, and methoxy substituents). This indicates that aromatic heterocycles or planar, conjugated guanidine/amidine/amide functional groups might also engage in favorable $\pi$-$\pi$ or cation-$\pi$ interactions with Phe residues in this subsite.

The binding conformation of the inhibitor's Lys residue identifies a potential new hydrogen bonding contact, while the position of the docked Met residue indicates new contacts and steric space that might be exploited. Finally, empirical results from deletion/addition experiments, corroborated by data from the mpp-RATKML binding mode, suggest that there is an optimal length for BoNT/A LC inhibitors. If an inhibitor is too short (for example, mpp-RAT), it does not occupy enough of the cleft, and consequently is not as potent; if it is too long (for example, mpp-RATKMLGSG), components that fit in the cleft do not contribute to activity. For the docked conformation of mpp-RATKML, the distance between the mpp phenyl and the terminal Leu is about 23 Å. Thus, preferred compounds of the present invention are about 15 Å to about 23 Å. Since amide bonds serve as mpp-RATKML pharmacophore planes, the compounds of the present invention may include bioisosteres such as carbenes, imines, and azo linkages.

5. Database Searches of Candidate Compounds

An initial three-dimensional search query incorporating all of the original pharmacophore components, in addition to the suggested components and criteria indicated above, identified no database hits. Consequently, combination search queries composed of 4 to 5 pharmacophore components were conducted. Of the numerous queries that were generated, the one that identified the four potent inhibitors included: (1) a pharmacophore component C that incorporated aromatic substituents (with and without heteroatoms), and planar, conjugated positive-ionizable functional groups; (2) a positive ionizable component, labeled F, to mimic the N$\zeta$ nitrogen of the mpp-RATKML Lys; (3) an increased distance range between pharmacophore planes A and B (about 6.5 to about 13 Å); (4) the inclusion of carbenes, imines, amides, and azo linkages as pharmacophore planes; and (5) a total compound length constraint of about 23 Å. The structures and $K_i$ values (determined in vitro) of the four inhibitors are shown in FIG. 1.

Molecular docking of the new inhibitors showed that they fit with good steric and hydropathic complementarity in the conformation of the BoNT/A LC that was used for mpp-RATKML docking. For NSC 341909, 308574, and 240898: (1) binding occurs down the length of the substrate cleft; (2) loop 1 serves as a solvent shield; (3) the planar, positive ionizable C components wedge between the side chain phenyls of Phe 162 and Phe193, with each engaging in a cation-$\pi$ interaction with the side-chain phenyl of Phe 193; (4) the positive ionizable F components engage in hydrogen bonds with the side chain carboxylate of Glu 54 (this is one of the hydrogen bonding interactions predicted for the Lys N$\zeta$ of docked mpp-RATKML, and with the side chain carboxylate of Glu 63, which, in the absence of a substituent mimicking the mpp-RATKML Arg guanidinium (pharmacophore component E, is free to turn in the opposite direction; and (5) a biaryl associated heteroatom is positioned such that it may interfere with the zinc catalytic engine.

Activity of Candidate Compounds

1. NSC 240898 Inhibits SNAP-25 Cleavage by BoNT/A in Living Neurons

The candidate compounds were assayed for neuronal uptake, toxicity, and protection. Chick spinal motor neurons were cultured by methods known in the art. See Kuhn, T B (2003) Methods. Cell Biol. 71:67-87, which is herein incorporated by reference. In brief, fertilized chicken eggs (SPAFAS/Charles River Laboratories, North Franklin, Conn.) were incubated at 37° C. for 6 days. Embryos were removed from the eggs and ventral spinal cords were isolated from the embryos. Cells were dissociated by trypsinization and trituration. Cells were preplated into a culture dish with Dullbecco's modified Eagle's medium plus 10% fetal bovine serum (FBS) for 1 hour to allow non-neuronal cells to attach to the dish, thereby increasing the percentage of neuronal cells in the suspension. Cells were centrifuged and resuspended in Leibovitz L15 medium (Gibco/Invitrogen, Carlsbad, Calif.) with N3 supplement and 10% FBS. The mitotic inhibitor 5-fluorodeoxyuridine was added to further reduce the population of non-neuronal (i.e. dividing) cells. Cells were plated into 6-well tissue culture plates that were coated first with poly-L-lysine, then with laminin. Cultures were incubated overnight at 37° C. prior to intoxication.

Autofluorescence was used to examine inhibitor entry into cells. Chick spinal motor neurons were incubated for 30 minutes with 20 μM inhibitor and examined for an increase in intracellular fluorescence on an inverted Nikon TE300 microscope with a standard DAPI filter set. Images were collected with a BioRad Radiance 2000 MP confocal/multiphoton system (Zeiss, Thornwood, N.Y.). For confocal images used to assay morphological indicators of general cell health after toxin and inhibitor treatments, spinal motor neuron cultures were fixed for 30 minutes in 3.7% formaldehyde and permeabilized in 0.2% Triton-X-100 for 10 minutes. After blocking for 30 minutes in 1% bovine serum albumin (BSA), cells were incubated with 1:500 DM1A anti-$\alpha$-tubulin (Sigma, St. Louis). Cells were then labeled with 1:500 Alexa 488 conjugated goat anti-mouse secondary antibody, 1:25 Texas red phalloidin, and Hoechst stain (Molecular Probes, Eugene, Oreg.).

NSC 341909, 308574, and 240898 were found to become concentrated within the cells in about 30 minutes.

Next, potential cytotoxic effects of the candidate compounds were assayed by incubating the cells with various concentrations of the NSC 341909, 308574, and 240898 for about 3.5 hours. Specifically, cells were pre-incubated with a candidate compound for 45 minutes, followed by 3.5 hours incubation with 10 nM BoNT/A (MetaBiologics Inc., Madison, Wis.) and the candidate compound. Cells were rinsed with fresh culture medium, scraped, collected, washed with PBS, lysed, and assessed for protein content using the Bradford protein assay (BioRad, Hercules, Calif.). Cell lysates were run on a 12% Tris-Glycine gel (Invitrogen, Carlsbad, Calif.), transferred to nitrocellulose, and probed with SMI 81 mouse anti-SNAP-25 (Sternberger Monoclonals Incorporated, Lutherville, Md.), and mouse anti-GAPDH (Covance Research Products, Inc., Berkeley, Calif.) primary antibodies. An HRP-conjugated goat anti-mouse secondary antibody was used (Pierce, Rockford, Ill.) in combination with an ECL Western blotting detection system (Pierce, Rockford, Ill.). Densitometry was performed using a UN-SCAN-IT gel automated digitizing system (Silk Scientific, Inc, Orem, Utah).

While NSCs 341909 and 308574 proved to be highly cytotoxic at concentrations as low as about 1 to about 5 μM, cells tolerated NSC 240898 at concentrations as high as about 40 μM. Specifically, as shown in FIG. 2A, cells treated with 40 μM NSC 240898 for about 3.5 hours, fixed, and stained to show tubulin, actin filaments, and DNA revealed little or no morphological signs of damage, e.g. collapsed growth cones, abnormal axonal varicosities, or blebbing.

Figure 2B:
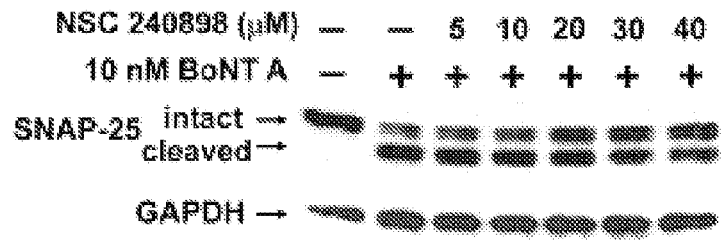
FIG. 2B is a Western blot revealing a dose-dependent NSC 240898 inhibition of BoNT/A SNAP-25 cleavage.
Figure 2C:
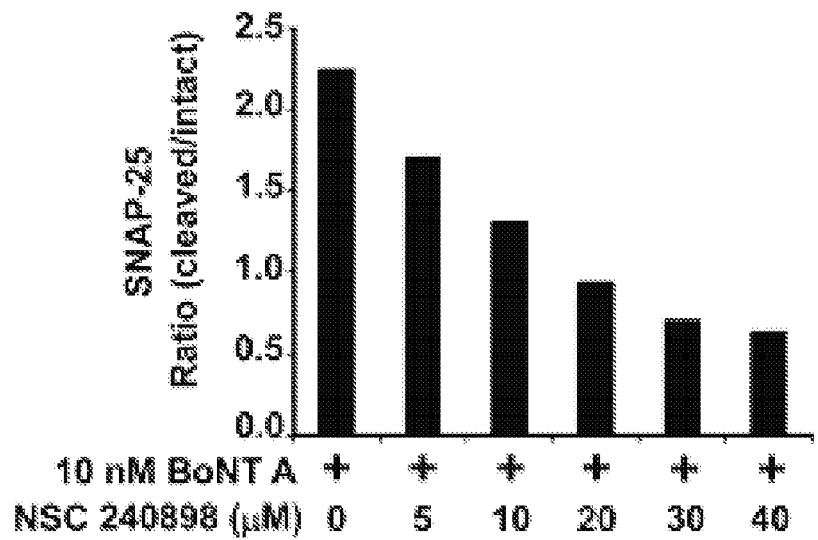
FIG. 2C provides the densitometric scans of the bands in the Western blot of FIG. 2B graphically as a ratio of cleaved to intact SNAP-25 for the concentrations of NSC 240898.

Pre-incubation of cells for about 30 to about 45 minutes with varying concentrations of NSC 240898, followed by intoxication with 10 nM BoNT/A in the continued presence of inhibitor, demonstrated a robust dose-dependent inhibition of SNAP-25 cleavage in Western blot analyses as shown in FIG. 2B and FIG. 2C. Thus, compounds of the present invention, such as NSC 240898 may be used to treat, prevent or inhibit BoNT/A intoxication in a subject.

Isothermal Titration Calorimetry

To confirm the specific nature of the NSC 240898:BoNT/A LC interaction, isothermal titration calorimetry (ITC) studies were performed using methods known in the art. Specifically, purified BoNT/A LC was subjected to a final gel filtration step (Superdex 200 column) to ensure a complete buffer exchange, as well as to exclude trace amounts of autocleavage products. All experiments were carried out in the same buffer to control for heat of dilution effects: 50 mM Hepes (pH 7.4) supplemented with 150 mM NaCl and 0.5 mM $ZnCl_2$. Concentrations of NSC 240898 solutions were confirmed by UV/Vis absorbance measurements. Calorimetric titration was performed multiple times on a VP-ITC calorimeter (MicroCal, Northhampton, Mass.) at 293 K. BoNT/A LC was used at a concentration of 28 µM in the ITC cell and inhibitor NSC 240898 at a concentration of 390 µM in the injection syringe. Prior to the titration, the samples were degassed for 10 minutes. The positive deflections observed at the end of the titration reflect the enthalpy of dilution of the inhibitor solution and were subtracted from the binding data. The first injection systematically showed a decreased enthalpy due to the technical limitations of the instrument and was omitted from curve fitting. The titration curve was then fit to a single site model by non-linear least squares regression as implemented by MicroCal Software Inc. in the Origin software package. According to this model, the parameters to be determined are: the number of binding sites (N), the binding enthalpy per site (ΔH), and the binding constant ($K_d$).

Table 2 shows measured and calculated thermodynamic values of NSC 240898 binding to the BoNT/A LC. The stoichiometry parameter (N) was adjusted in the fit in order to account for uncertainties in the concentration of protein in solution.

TABLE 2

| Temperature (° C.) | 20 |
|---|---|
| N | 0.83 ± 0.04 |
| $K_a$ (M$^{-1}$) | 2.18 × 10$^5$ ± 4.5 × 10$^4$ |
| Kd (µM) | 4.6 |
| ΔH (kcal mol$^{-1}$) | −3.04 ± 0.20 |
| ΔS (cal mol$^{-1}$ K$^{-1}$) | 14.0 |

Figure 3A:
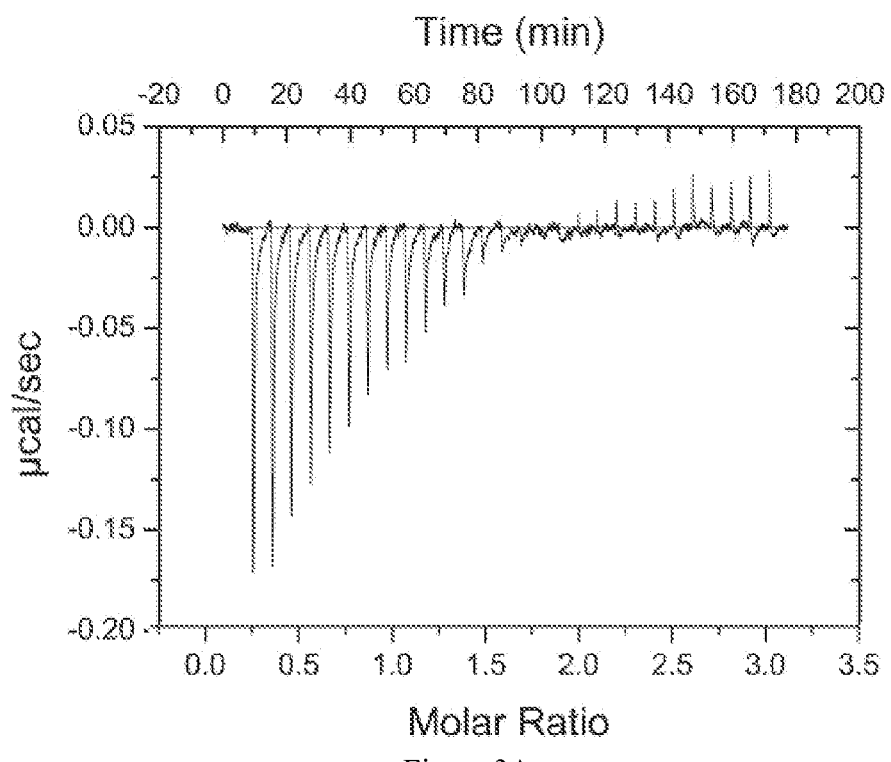
FIGS. 3A-3B are graphs of the isothermal titration calorimetry (ITC) of the NSC 240848:BoNT/A LC interaction.
Figure 3B:
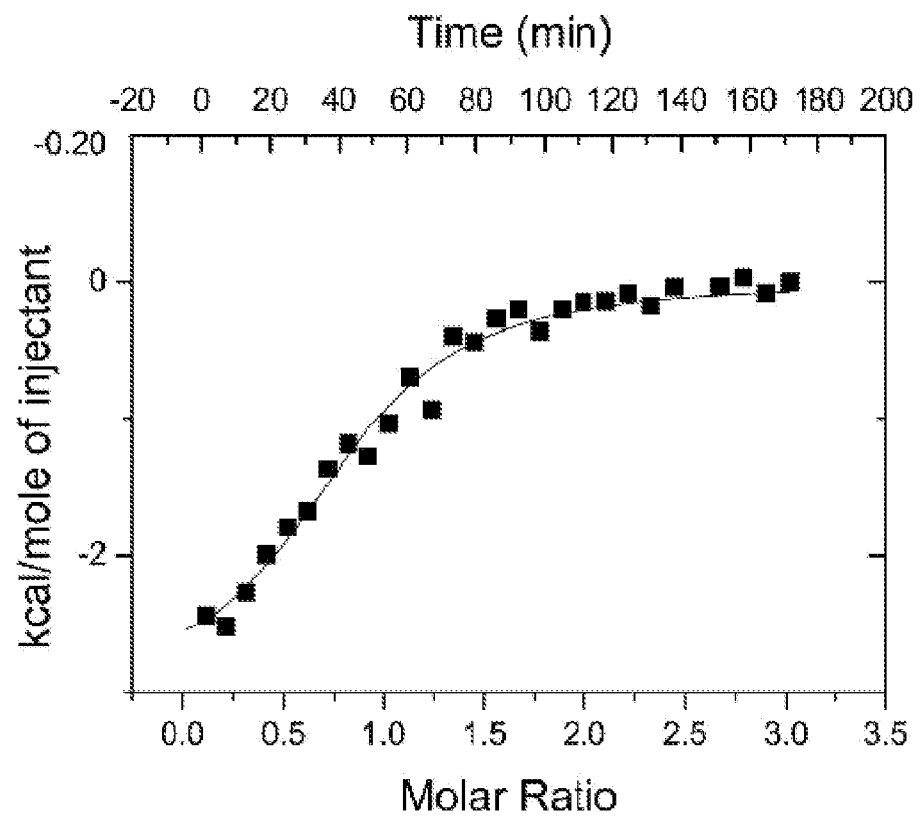

Representative data are shown in FIGS. 3A-3B. A low affinity binding event ($K_d$~4.6 µM) that was largely entropy-driven (ΔS=14 cal/mol K) was observed; comparatively, the enthalpic contribution was relatively low (ΔH=−3.04 kcal/mol). Thus, affinity of the small molecule compounds of the present invention may be significantly improved by optimizing electrostatic interactions with surrounding enzyme residues.

Due to the low affinity of the interaction, a large excess of NSC 240898 was necessary to drive the titration to saturation. While enzymatic assays and molecular dynamics simulations indicate the number of NSC 240898 binding sites to be one, this parameter was adjusted in the fit in order to account for uncertainties in the concentration of protein in solution. Subsequently, N=0.83±0.04 was obtained, which is consistent with a 1:1 stoichiometry (along with a small fraction of misfolded protein as often observed in ITC experiments).

The significant entropic contribution observed suggests a burial of hydrophobic surfaces and the release of solvent upon inhibitor binding, consistent with the hydrophobic nature of NSC 240898. Taking into account the conformational variability of loops 1, 3 and 4 of the BoNT/A LC this solvent release is probably accompanied by a conformational change in at least one of the flexible loops.

NSC 328398

NSC 328398 is a novel scaffold that was discovered using a different three-dimensional search query that was based on the refined pharmacophore, and exhibited 45% inhibition of BoNT/A LC metalloprotease activity at 10 µM.

NSC 328398
45% BoNT/A LC inhibition (10 µM)

New Small Molecule Compounds

Other small molecule compounds which were identified according to the methods disclosed herein to inhibit BoNT/A LC metalloprotease activity are provided in Table 3.

TABLE 3

| NSC | Structure | % Inhibition |
|---|---|---|
| 341909 | 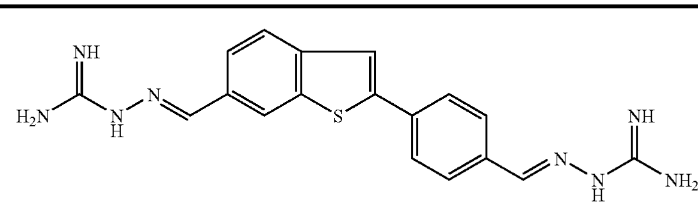 | 68% |

TABLE 3-continued

| NSC | Structure | % Inhibition |
| --- | --- | --- |
| 308574 | 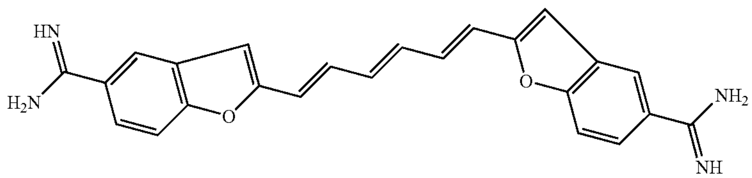 | 63% |
| 240898 | 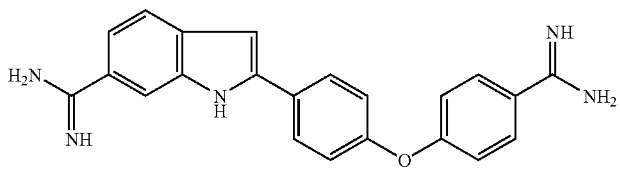 | 64% |
| 341907 | 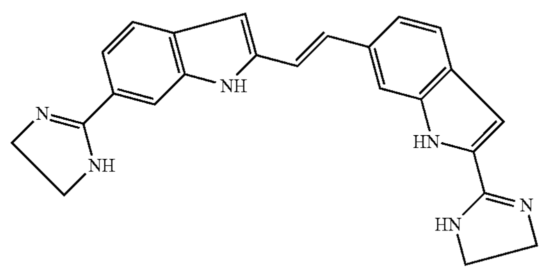 | 60% |
| 266472 | 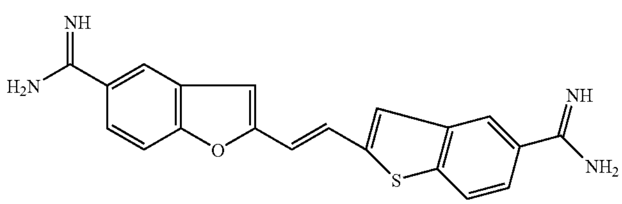 | 57% |
| 330690 | 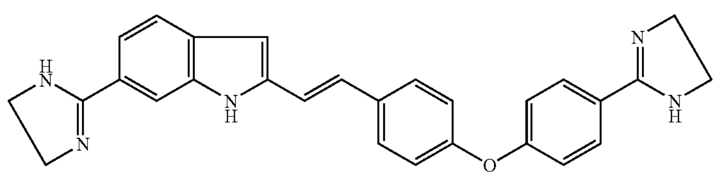 | 53% |
| 278999 | 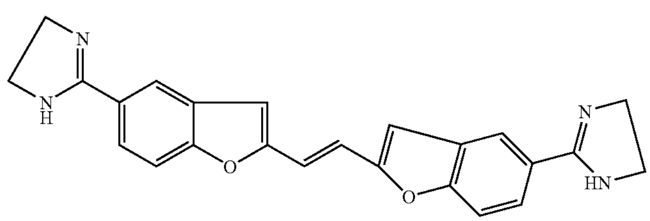 | 53% |
| 308571 | 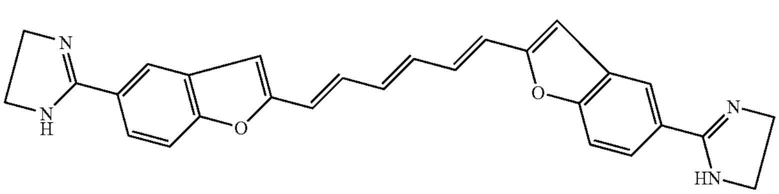 | 52% |

TABLE 3-continued

| NSC | Structure | % Inhibition |
|---|---|---|
| 290107 | 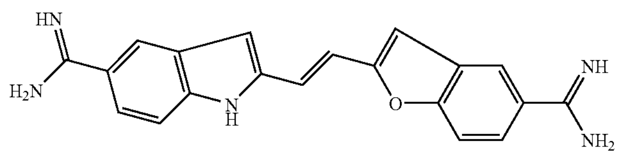 | 52% |
| 290108 | 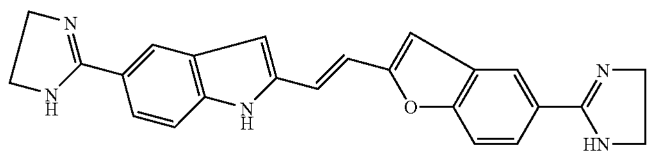 | 51% |
| 294209 | 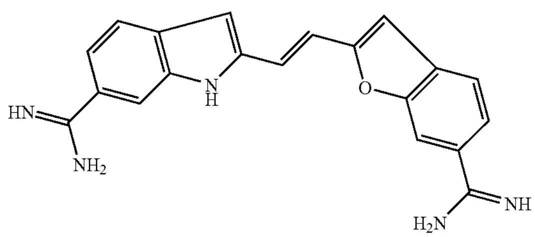 | 48% |
| 317884 | 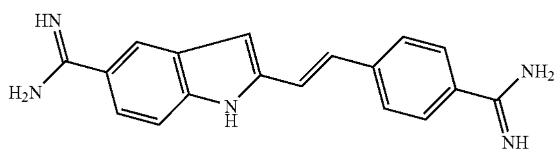 | 47% |
| 294203 | 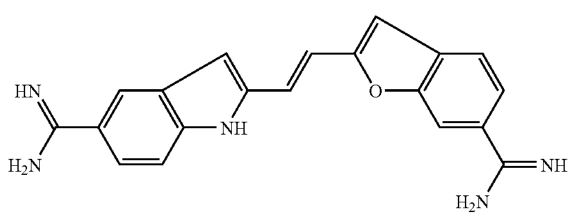 | 46% |
| 294494 | 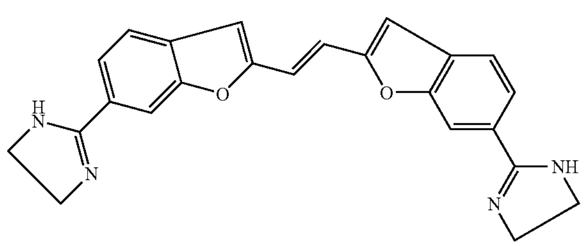 | 45% |
| 317881 | 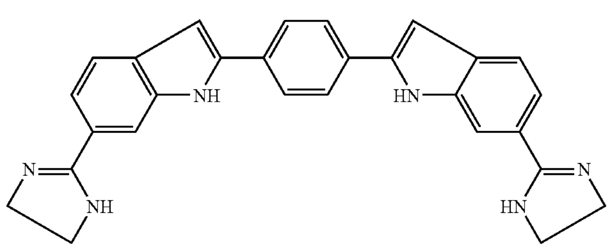 | 45% |

TABLE 3-continued

| NSC | Structure | % Inhibition |
|---|---|---|
| 330688 | 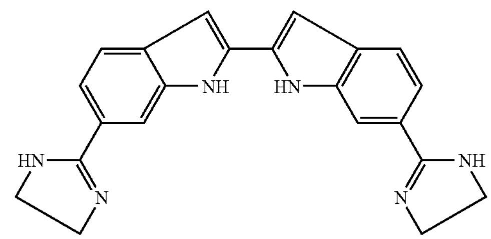 | 43% |
| 317886 | 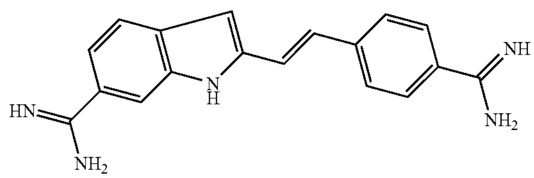 | 43% |
| 317883 | 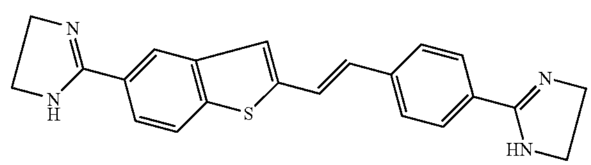 | 41% |
| 352341 | 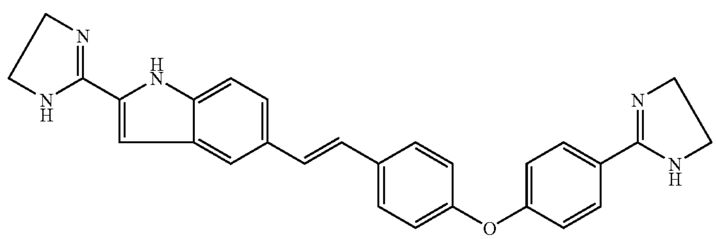 | 40% |
| 294204 | 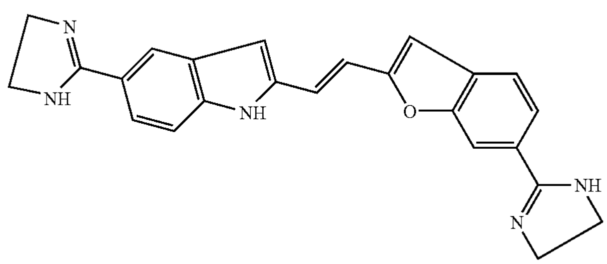 | 38% |
| 341911 | 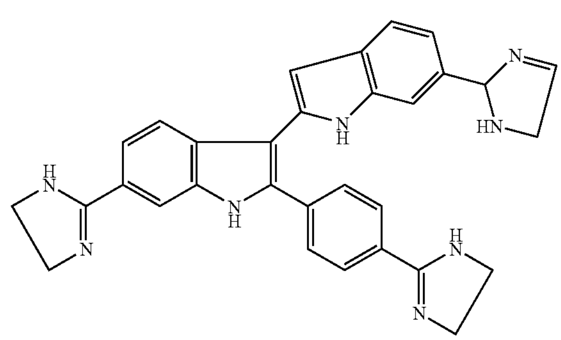 | 37% |

TABLE 3-continued
| NSC | Structure | % Inhibition |
|---|---|---|
| 300511 | 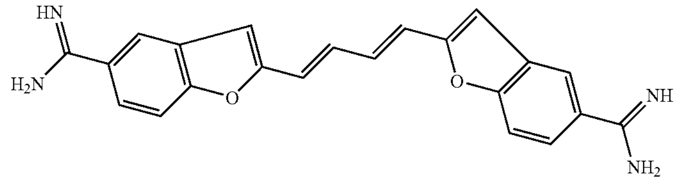 | 37% |
| 607617 | 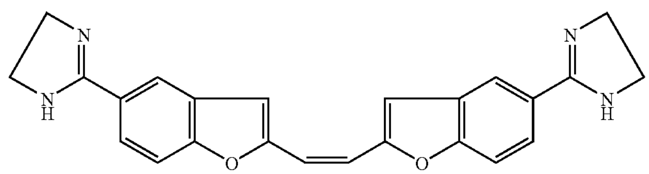 | 36% |
| 294202 | 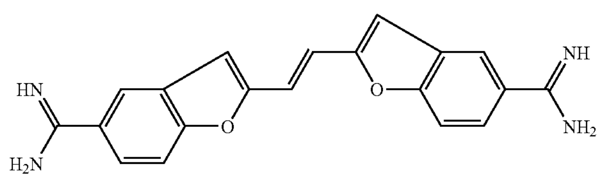 | 35% |
| 317880 | 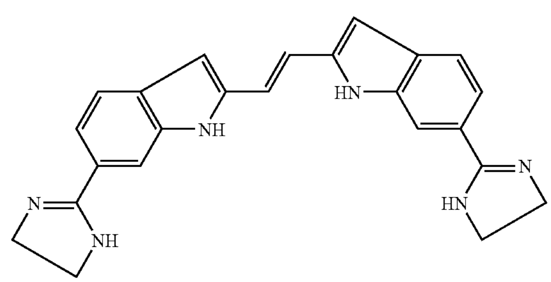 | 35% |
Thus, compounds of the present invention have the following structural formula:
where Y is
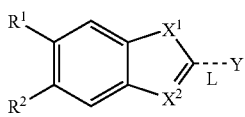
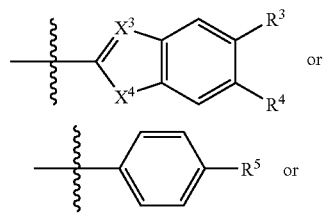
-continued
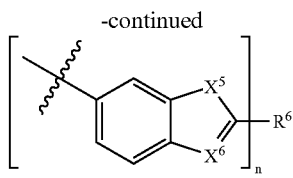
wherein
n is 1 or 2;
$X^1, X^2, X^3, X^4, X^5$ and $X^6$ are each independently N, S, O, $SO_2$, $CR^7$ or $NR^8$ and at least one of $X^1$ or $X^2$ is N, S, O, $SO_2$, or $NR^8$;
L is a linker which may be a direct bond or
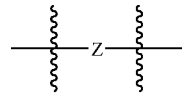

where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate; and $R^8$ is hydrogen, OH, a halogen, or an optionally substituted alkyl.

It is noted that in the structural formulas of the present invention, the bond orders of the specified rings may vary when the various heteroatoms introduce specific requirements to satisfy aromaticity, prevent antiaromaticity, and stabilize tautomeric forms due to localization. Thus, the appropriate bond orders of the ring structures in the structural formulas of the present invention are contemplated herein.

In some embodiments, $R^1$ is hydrogen, amidine, 2-imidazoline, amino, guanidine, methyl, aminomethyl-hydroxamine, or methylamine-guanidine.

In some embodiments, $R^2$ is hydrogen, amidine, 2-imidazoline, amino, guanidine, methyl, aminomethyl-hydroxamine, or methylamine-guanidine.

In some embodiments, $R^3$ is hydrogen, amidine, 2-imidazoline, amino, guanidine, methyl, aminomethyl-hydroxamine, or methylamine-guanidine.

In some embodiments, $R^4$ is hydrogen, amidine, 2-imidazoline, amino, guanidine, methyl, aminomethyl-hydroxamine, or methylamine-guanidine.

In some embodiments, $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine.

In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole.

In some embodiments, $X^1$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^3$ is N, NH, S, O, $SO_2$, or CH.
In some embodiments, $X^4$ is N, NH, S, O, $SO_2$, or CH.
In some embodiments, $X^5$ is N, NH, S, O, $SO_2$, or CH.
In some embodiments, $X^6$ is N, NH, S, O, $SO_2$, or CH.

In some embodiments, at least one of $R^1$, $R^2$, $R^3$, $R^4$, $R^5$, $R^6$ or $R^7$ is —H, —$CH_3$,

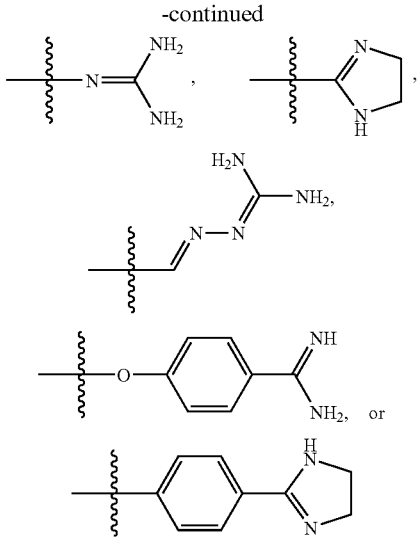

In some embodiments, $R^5$ is —$NH_2$,

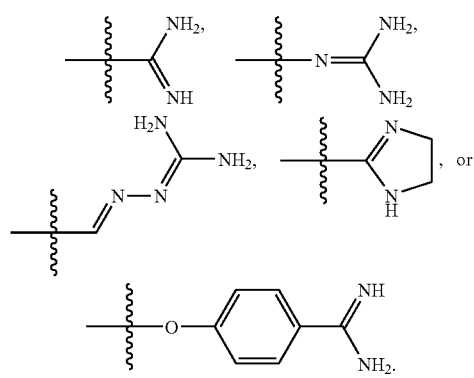

In some embodiments, $R^6$ is

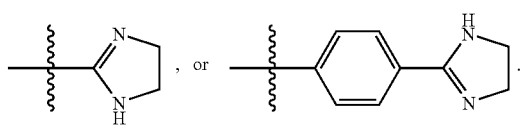

In some embodiments, $R^7$ is —H, —$CH_3$, —$NH_2$,

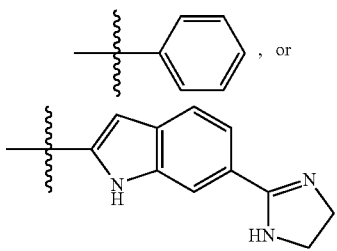

In some embodiments, $R^8$ is —H, —$(CH_2)_2OH$, or —$(CH_2)_2Cl$.

In some embodiments, L is a direct bond,

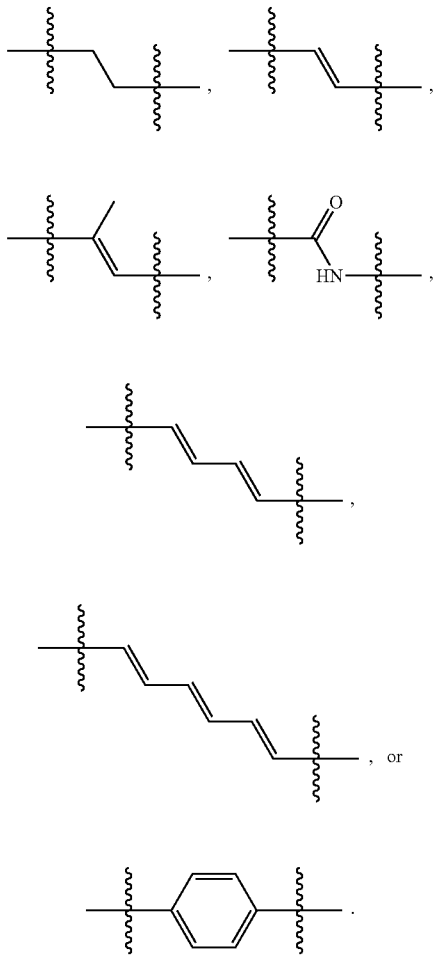

In some embodiments, compounds of the present invention have the following structural formulae:

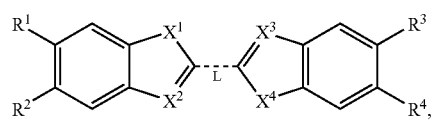
(A)

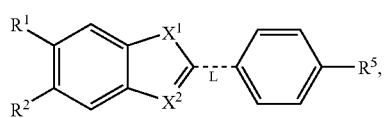
(B)

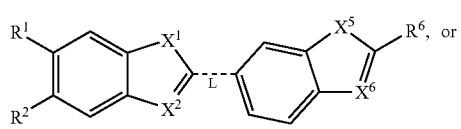
(C)

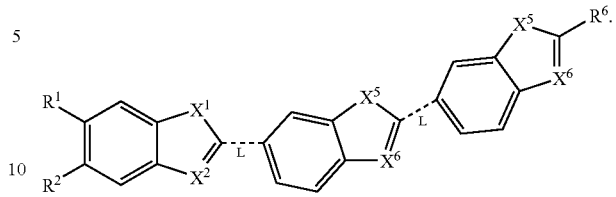
(D)

wherein
n is 1 or 2;
$X^1, X^2, X^3, X^4, X^5$ and $X^6$ are each independently N, S, O, $SO_2$, $CR^7$ or $NR^8$ and at least one of $X^1$ or $X^2$ is N, S, O, $SO_2$, or $NR^8$;

L is a linker which may be a direct bond or

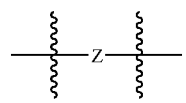

where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate; and $R^8$ is hydrogen, OH, a halogen, or an optionally substituted alkyl.

In some embodiments, the compound is NSC 92833, NSC 103699, NSC 103701, NSC 130681, NSC 240890, NSC 240891, NSC 240893, NSC 240894, NSC 240895, NSC 240896, NSC 240897, NSC 240898, NSC 240899, NSC 240900, NSC 266472, NSC 266474, NSC 266475, NSC 266476, NSC 266477, NSC 266482, NSC 278995, NSC 278996, NSC 278997, NSC 278999, NSC 290107, NSC 290108, NSC 290109, NSC 290111, NSC 291103, NSC 294199, NSC 294200, NSC 294201, NSC 294202, NSC 294203, NSC 294204, NSC 294206, NSC 294207, NSC 294208, NSC 294494, NSC 300509, NSC 300510, NSC 300511, NSC 300512, NSC 302569, NSC 308569, NSC 308570, NSC 308571, NSC 308572, NSC 308573, NSC 308574, NSC 317880, NSC 317881, NSC 317883, NSC 317884, NSC 317885, NSC 317886, NSC 317887, NSC 328398, NSC 330687, NSC 330688, NSC 330689, NSC 330690, NSC 341082, NSC 341907, NSC 341909, NSC 341910, NSC 341911, NSC 352341, NSC 369718, NSC 369721, NSC 607617, or NSC 12155. The structural formulas of these compounds are known in the art and may be obtained from various sources including the World Wide Web at dtp.nci.nih.gov/dtpstandard/ChemData/index.jsp and ncbi.nlm.nih.gov/entrez/query.fcgi?CMD=&DB=PubMed and are herein incorporated by reference.

Derivatives of NSC 240898 and Synthesis Thereof

Compounds of the present invention may be synthesized using methods known in the art. For example, compounds which are structurally similar to NSC 240898, such as those shown in Table 1, may be synthesized as provided herein.

TABLE 1

| No. | $R^a$ and $R^b$ | X | Y | MW | CLogP | HBA | HBD | DRF |
|---|---|---|---|---|---|---|---|---|
| 14 | CN | NH | CH | 335.36 | 5.58 | 4 | 1 | 5 |
| 15 | CN | NH | N | 336.35 | 4.35 | 5 | 1 | 5 |
| 16 | CN | O | CH | 352.41 | 6.31 | 3 | 0 | 5 |
| 17 | CN | O | N | 353.40 | 5.04 | 4 | 0 | 5 |
| 18 | $CONH_2$ | NH | CH | 371.39 | 3.55 | 4 | 3 | 5 |
| 19 | $CONH_2$ | NH | N | 372.38 | 2.31 | 5 | 3 | 5 |
| 20 | $CONH_2$ | O | CH | 388.44 | 4.52 | 3 | 2 | 5 |
| 21 | $CONH_2$ | O | N | 389.43 | 3.25 | 4 | 2 | 5 |
| 22 | $C(=NH)NH_2$ | NH | CH | 369.42 | 3.39 | 6 | 5 | 5 |
| 23 | $C(=NH)NH_2$ | NH | N | 370.41 | 2.21 | 7 | 5 | 5 |
| 24 | $C(=NH)NH_2$ | O | CH | 386.47 | 4.47 | 5 | 4 | 5 |
| 25 | $C(=NH)NH_2$ | O | N | 387.46 | 3.21 | 6 | 4 | 5 |

Also recorded in Table 1 are Lipinski's "drug-like" guidelines for these compounds; molecular weight<500 kda, low lipophilicity (cLogP<5), less than 5 hydrogen bond donors, less than 10 hydrogen bond acceptors. See Lipinski, et al. (2001) Adv. Drug. Deliv. Rev. 46:3-26, which is herein incorporated by reference.

The compounds in Table 1 may be synthesized according to Scheme A, parts A-D as follows:

Scheme 1. Specific Example of the Synthesis of an NCS 240898 Analog

A. Pd-Catalyzed Aromatic Substitution

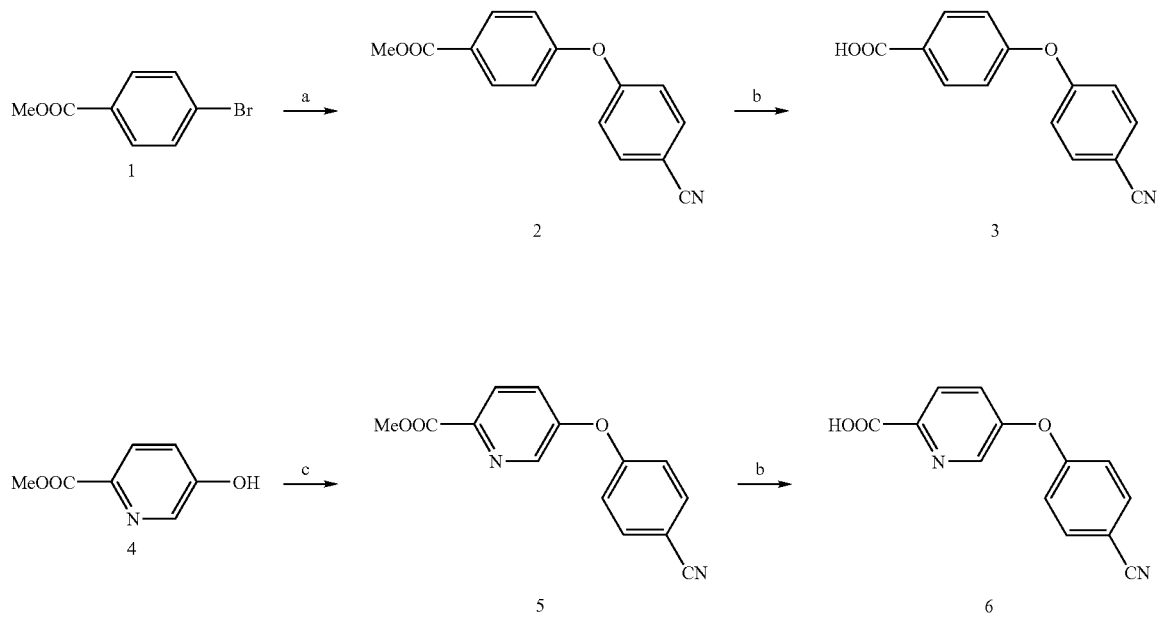

Reagents and Conditions: a) 4-cyanophenol, Pd (II). b) LiOH. c) 4-fluorobenzonitrile, base.

-continued

B. Indole Synthesis with Intermediates 3 and 6

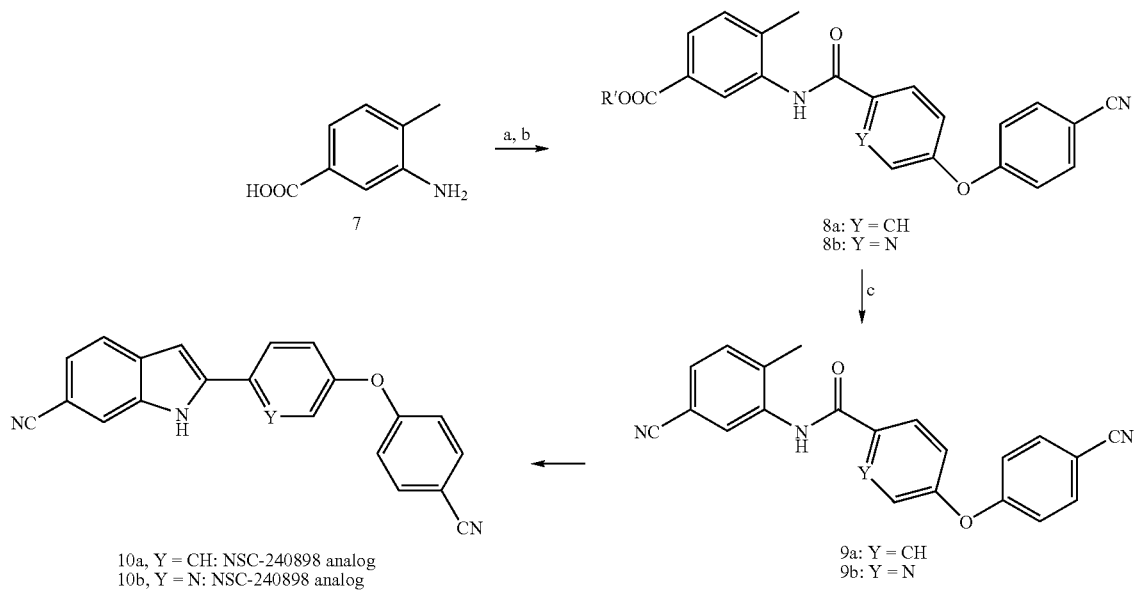

10a, Y = CH: NSC-240898 analog
10b, Y = N: NSC-240898 analog

8a: Y = CH
8b: Y = N

9a: Y = CH
9b: Y = N

Reagents and Conditions: a) esterification. b) coupling with 3 or 6. c) Me$_2$AlNH$_2$. d) LDA, —H$_2$O C. Benzothiophene Synthesis

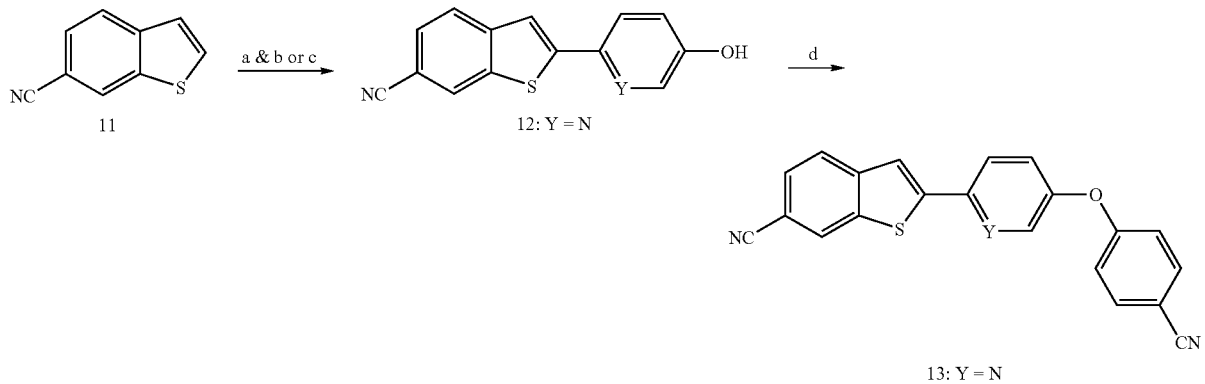

11

12: Y = N

13: Y = N

Reagents and Conditions: a) bis(pinacolato)boron, IrCl(Cyclopentadiene)$_2$. b) 6-chloropyridin-3-ol, Pd(II), base. c) LDA, then 6-chloropyridin-3-ol. d) 4-fluorobenzonitrile, base.

D. R Group Transformations

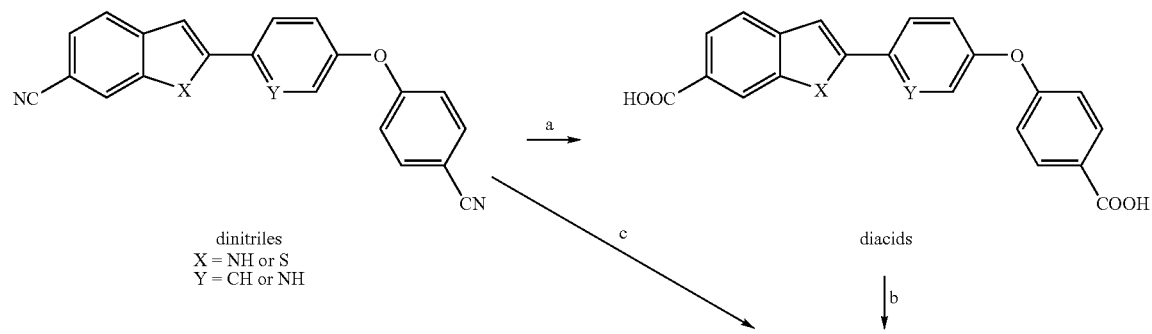

dinitriles
X = NH or S
Y = CH or NH diacids

-continued

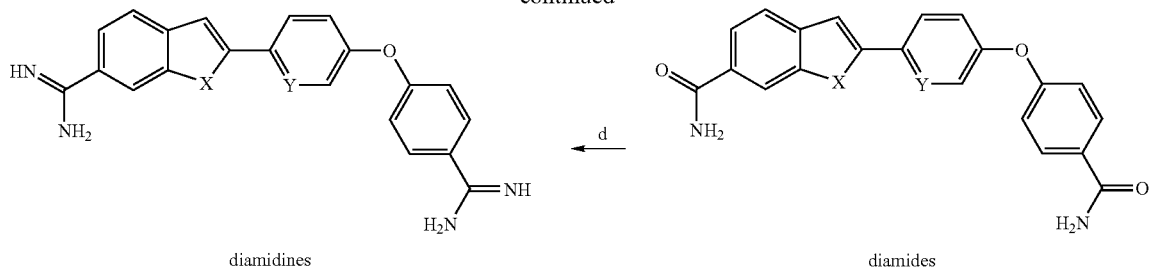

diamidines diamides

Reagents and Conditions: a) $H_2O$, $H_2SO_4$. b) $SOCl_2$, then $NH_3$. c) $H_2SO_4$ or KOH, t-BuOH. d) Lawessen's reagent with MeI, then $NH_3$.

As shown in Scheme 1, Part A, methyl 4-bromobenzoate (1) is treated with 4-cyanophenol in the presence of a palladium (II) catalyst to produce the diphenyl ether 2, which is then hydrolyzed to give 4-(4-cyanophenoxy)benzoic acid (3). See Aranyos et al. (1999) J Am Chem Soc 121:4369; and Mann et al. (1999) J Am Chem Soc 121:3224, which are herein incorporated by reference. Compound 3 can then serve as a partner with 3-amino-4-methylbenzoic acid (7) to provide the necessary substrate for a modified Madelung indole synthesis (Part B). Esterification of 7 followed by coupling with benzoic acid 3 will provide benzamide 8a, which, upon treatment with dimethylaluminum amide, will give the corresponding nitrile 9a. See Theodre & Nelson (1987) J Org Chem 52:1309; and Wood et al. (1979) Tetrahedron Lett 20:4907-4910, which are herein incorporated by reference. Exposure of 9a to lithium diisopropylamide will then effect a dehydrative cyclization to produce the NSC 240898 analog, e.g. compound 10a. See Houlihan et al. (1981) J Org Chem 46:4511, 4515, which is herein incorporated by reference. Likewise, analog 10b can be synthesized in an analogous fashion, as indicated in Parts A and B. Note that the addition of a nitrogen atom in the central ring may enhance zinc binding, since the site of coordination for the zinc will now become bidentate. An alternative plan to produce compounds 10, not shown here, is to use a Fischer indole synthesis protocol. See Robinson, B. (1983) The Fischer Indole Synthesis. Wiley, New York.; and Sundberg, R. J. (1970) The Chemistry of Indoles. Academic Press, New York, pp. 142-163, which are herein incorporated by reference.

Synthesis of one example of the proposed inhibitors shown in the Synthetic Analysis, where X═S and Y═N is also shown in Scheme 1 (Part C). 6-Cyanobenzo[b]thiophene (11) is coupled with 6-chloro-3-pyridinol to produce intermediate 12, using either an iridium catalyst and bis(pinacolato)boron to prepare 6-cyanobenzo[b]thiophene-2-boronic acid, and then using this boronic acid in a palladium catalyzed Suzuki coupling with 6-chloro-3-pyridinol; or, by generating the anion at the 2-position of 11 with lithium diisopropylamide and quenching this anion with 6-chloropyridin-3-ol. See U.S. Patent Publication 20050148775; and Guiles et al. (1996) J Org Chem 61:5169, which are herein incorporated by reference. Subsequent conversion of intermediate 12 to target compound 13 can then be accomplished by nucleophilic aromatic substitution, by treating the anion of 12 with 4-fluorobenzonitrile. Note that compound 13, where Y═CH, can be prepared in an analogous fashion. Since sulfur is a very good coordinating ligand for zinc, it is expected that compound 13 and compounds derived from compound 13 could provide excellent inhibitors of the BoNT/A LC metalloproteinase.

Compounds of general structure 10 and 13 are very versatile compounds. In addition to being target compounds themselves, they are portals to the preparation of a wide variety of additional compounds. As shown in Scheme 1, Part D, the dinitriles can readily be converted to the diacids, by hydrolysis under acidic conditions. These diacids are also very versatile, dual point compounds. The diacids will be converted to the simple diamides by preparing the diacid chlorides and quenching them with ammonia. Alternatively, if one chooses to avoid the diacids as discreet intermediates, we will treat the dinitriles directly with sulfuric acid or with potassium hydroxide to hydrate the nitrile groups and produce the diamides in one step. See Sarel & Newman (1956) J Am Chem Soc 78:5416; and Hall & Gisler (1976) J Org Chem 41:3769, which are herein incorporated by reference. The diamides, in turn, will be converted to the diamidines by treatment with Lawessen's reagent followed by S-methylation, and subsequent treatment of these activated intermediates with ammonia. See Yde, et al. (1984) Tetrahedron Lett 40:2047, which is herein incorporated by reference. Note that all of the general structures shown in Scheme 1 are quite versatile in their reactivities and potential transformations, and the transformations shown are only a selected few from those transformations that can be performed. Also note that specific compounds chosen for display in Table 1 are all covered by the general structures.

Preferred compounds of the present invention also include those which are structurally related to NSC341909, NSC 308574, and Q2-15, such as the following:

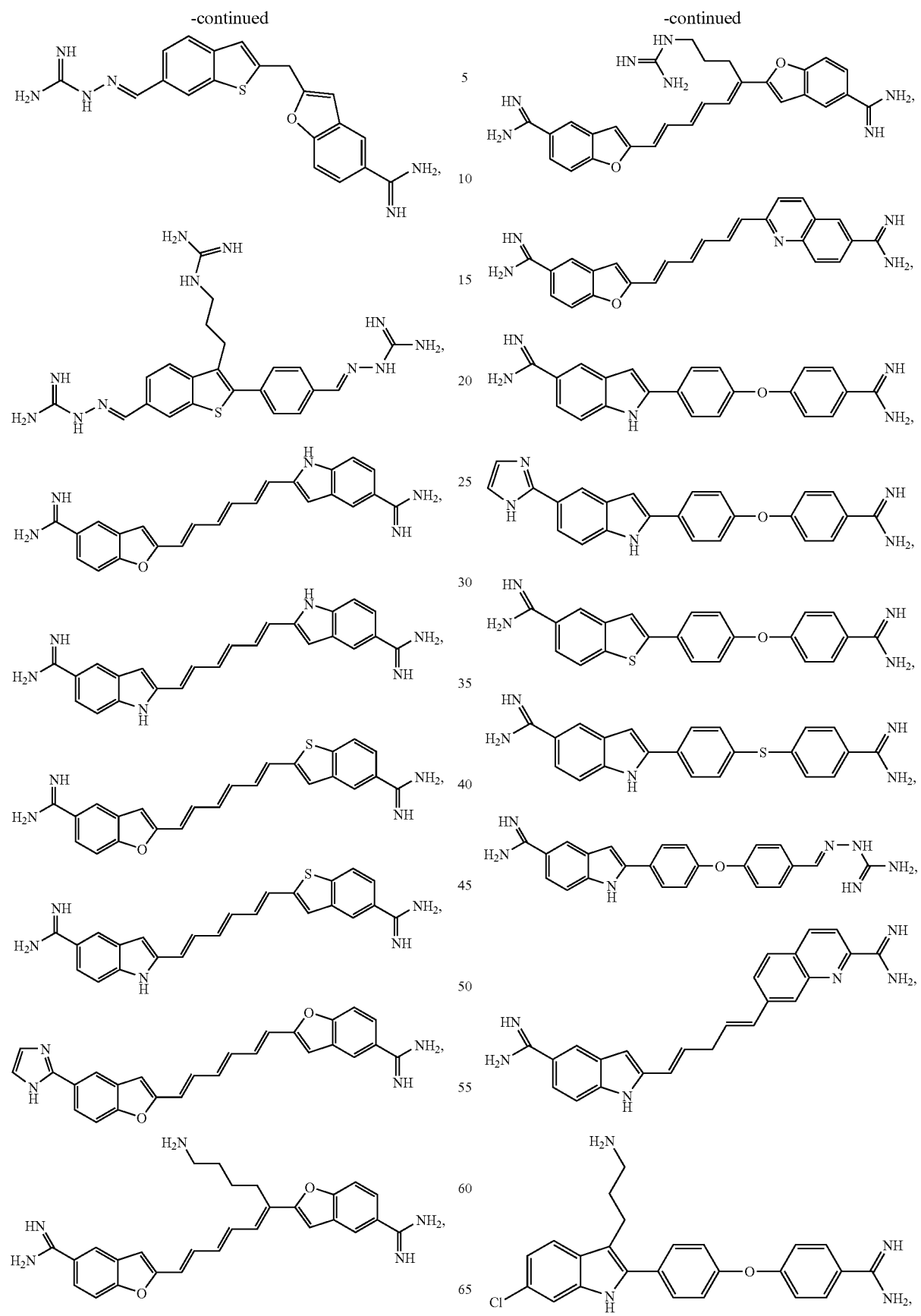

-continued

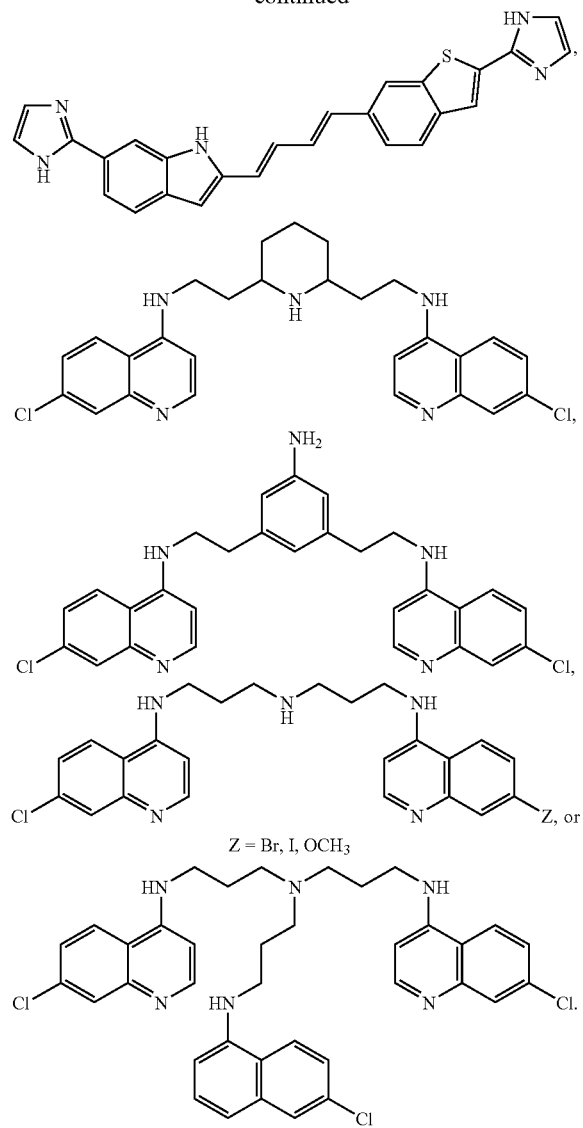

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

A "halo" or "halogen" means fluorine, bromine, chlorine, and iodine.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), and the like, which may be unsubstituted (i.e., contain only carbon and hydrogen) or substituted by one or more suitable substituents as defined below. A "lower alkyl group" is intended to mean an alkyl group having from 1 to 8 carbon atoms in its chain.

A "haloalkyl" refers to an alkyl that is substituted with one or more same or different halo atoms, e.g., —$CH_2Cl$, —$CF_3$, —$CH_2CF_3$, —$CH_2CCl_3$, and the like.

An "alkenyl" means straight and branched hydrocarbon radicals having from 2 to 8 carbon atoms and at least one double bond such as ethenyl, 3-buten-1-yl, 2-ethenylbutyl, 3-hexen-1-yl, and the like. The term "alkenyl" includes, cycloalkenyl, and heteroalkenyl in which 1 to 3 heteroatoms selected from O, S, N or substituted nitrogen may replace carbon atoms.

An "alkynyl" means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

A "cycloalkyl" is intended to mean a non-aromatic monovalent monocyclic or polycyclic radical having from 3 to 14 carbon atoms, each of which may be saturated or unsaturated, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of cycloalkyl groups include cyclopropyl, cycloheptyl, cyclooctyl, cyclodecyl, cyclobutyl, adamantyl, norpinanyl, decalinyl, norbornyl, cyclohexyl, and cyclopentyl.

A "heterocycloalkyl" is intended to mean a non-aromatic monovalent monocyclic or polycyclic radical having 1-5 heteroatoms selected from nitrogen, oxygen, and sulfur, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of heterocycloalkyl groups include oxiranyl, pyrrolidinyl, piperidyl, tetrahydropyran, and morpholinyl.

An "aryl" (Ar) is intended to mean an aromatic monovalent monocyclic or polycyclic radical comprising generally between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

A "heteroaryl" is intended to mean an aromatic monovalent monocyclic or polycyclic radical comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

A "hydroxy" is intended to mean the radical —OH.

An "alkoxy" is intended to mean the radical —OR, where R is an alkyl group. Exemplary alkoxy groups include methoxy, ethoxy, propoxy, and the like.

A "hydroxyalkyl" means an alkyl that is substituted with one, two, or three hydroxy groups, e.g. hydroxymethyl, 1 or 2-hydroxyethyl, 1,2-, 1,3-, or 2,3-dihydroxypropyl, and the like.

A "haloalkoxy" refers to an —O-(haloalkyl) group. Examples include trifluoromethoxy, tribromomethoxy, and the like.

A "cycloalkoxy" is intended to mean the radical —OR, where R is a cycloalkyl or heterocycloalkyl group.

An "aryloxy" is intended to mean the radical —OR, where R is an aryl or heteroaryl group. Examples include phenoxy, pyridinyloxy, furanyloxy, thienyloxy, pyrimidinyloxy, pyrazinyloxy, and the like.

An "acyl" is intended to mean a —C(O)—R radical, where R is an alkyl or aryl, bonded through a carbonyl group. Acyl groups include acetyl, benzoyl, and the like.

An "aralkyl" means an alkyl that is substituted with an aryl group. Examples include —$CH_2$-phenyl, —$(CH_2)_2$-phenyl, —$(CH_2)_3$-phenyl, —$CH_3CH(CH_3)CH_2$-phenyl, and the like.

A "heteroaralkyl" group means an alkyl that is substituted with a heteroaryl group. Examples include —$CH_2$-pyridinyl, —$(CH_2)_2$-pyrimidinyl, —$(CH_2)_3$-imidazolyl, and the like.

A "carboxy" is intended to mean the radical —C(O)OH.

An "alkoxycarbonyl" is intended to mean the radical —C(O)OR, where R is an alkyl group. Examples include methoxycarbonyl, ethoxycarbonyl, and the like.

An "amino" is intended to mean the radical —$NH_2$.

An "amine with stabilized carbocations" are comprised of two or more $NH_2$ groups that contribute lone pairs to configure a highly stabilized carbocation. Examples include amidines and guanidines.

An "alkylamino" is intended to mean the radical —NHR, where R is an alkyl group or the radical —$NR^aR^b$, where $R^a$ and $R^b$ are each independently an alkyl group. Examples of alkylamino groups include methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino, N-n-hexyl-N-methylamino and the like.

An "alkylsulfhydryl" is intended to mean R—SH, where R is an alkyl group. Examples include methylsulfhydryl, ethylsulfhydryl, n-propylsulfhydryl, iso-propylsulfhydryl, n-butylsulfhydryl, iso-butylsulfhydryl, secondary-butylsulfhydryl, tertiary-butylsulfhydryl. Preferable alkylsulfhydryl groups are methylsulfhydryl, ethylsulfhydryl, n-propylsulfhydryl, n-butylsulfhydryl, and the like.

An "alkylhydroxymate" is intended to mean the radical R—C(O)NH—OH, where R is an alkyl group. Examples include methylhydroxymate, ethylhydroxymate, n-propylhydroxymate, iso-propylhydroxymate, n-butylhydroxymate, iso-butylhydroxymate, secondary-butylhydroxymate, tertiary-butylhydroxymate. Preferable alkylhydroxymate groups are methylhydroxymate, ethylhydroxymate, n-propylhydroxymate, n-butylhydroxymate, and the like. A "carbamoyl" is intended to mean the radical —C(O)$NH_2$.

A "carbamoyl" is intended to mean the radical —C(O)$NH_2$.

An "alkylaminocarbonyl" is intended to mean the radical —C(O)NHR, where R is an alkyl group or the radical —C(O)$NR^aR^b$, where $R^a$ and $R^b$ are each independently an alkyl group. Examples include methylaminocarbonyl, ethylaminocarbonyl, dimethylaminocarbonyl, methylethylaminocarbonyl, and the like.

A "mercapto" is intended to mean the radical —SH.

An "alkylthio" is intended to mean the radical —SR, where R is an alkyl or cycloalkyl group. Examples of alkylthio groups include methylthio, ethylthio, n-propylthio, isopropylthio, tert-butylthio, n-pentylthio, n-hexylthio, cyclopropylthio, cyclobutylthio, cyclopentylthio, cyclohexylthio, and the like.

An "arylthio" is intended to mean the radical —SR, where R is an aryl or heteroaryl group. Examples include phenylthio, pyridinylthio, furanylthio, thienylthio, pyrimidinylthio, and the like.

A "thioacyl" is intended to mean a —C(S)—R radical, where R is an alkyl or aryl, bonded through a thiol group.

An "alkylsulfonyl" is intended to mean the radical —$SO_2R$, where R is an alkyl group. Examples include methylsulfonyl, ethylsulfonyl, n-propylsulfonyl, iso-propylsulfonyl, n-butylsulfonyl, iso-butylsulfonyl, secondary-butylsulfonyl, tertiary-butylsulfonyl. Preferable alkylsulfonyl groups are methylsulfonyl, ethylsulfonyl, n-propylsulfonyl, n-butylsulfonyl, and the like.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, $3^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as a halogen; $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both when they contain one or more stereogenic centers as designated by R or S according to the Cahn-Ingold-Prelog rules whether the absolute or relative configuration is known. All such single stereoisomers, racemates and mixtures thereof are intended to be within the scope of the present invention.

Some of the compounds in the present invention may exist as geometric isomers as the result of containing a stereogenic double bond. In such cases, they may exist either as pure or mixtures of cis or trans geometric isomers or (E) and (Z) designated forms according to the Cahn-Ingold-Prelog rules and include compounds that adopt a double bond configuration as a result of electronic delocalization.

As generally understood by those skilled in the art, an optically pure compound having one or more chiral centers (i.e., one asymmetric atom producing unique tetrahedral configuration) is one that consists essentially of one of the two possible enantiomers (i.e., is enantiomerically pure), and an optically pure compound having more than one chiral center is one that is both diastereomerically pure and enantiomerically pure. If the compounds of the present invention are made synthetically, they may be used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to binding site interactions. Provision of such multivalent forms of active binding compounds with optimal spacing between the binding site moieties may enhance binding site interactions. See e.g. Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound, or a compound that is biologically active with respect to the intended pharmacodynamic effect. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., *J. Pharm. Sci.*, 86(7):765-767; Bagshawe K., (1995) Drug Dev. Res. 34:220-230; Bodor, N., (1984) Advances in Drug Res. 13:224-331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention are useful in inhibiting BoNT/A LC metalloprotease activity. The compounds of the present invention are also useful in treating, inhibiting or preventing intoxication caused by botulinum toxin in a subject. Further, since some of the compounds of the present invention are found to exhibit antibacterial activity, the compounds of the present invention are useful in inhibiting, reducing or preventing growth of or destroying bacteria of at least one bacterial strain. The compounds of the present invention are also useful in treating, inhibiting or preventing an infection caused by bacterial of at least one bacterial strain in a subject. The bacteria belong to various gram positive and gram negative bacteria strains including *Bacillus, Burkholderia, Enterobacter, Escherichia, Helicobacter, Klebsiella, Mycobacterium, Neisseria, Pseudomonas, Staphylococcus, Streptococcus, Yersinia* and the like, including drug resistance strains. In preferred embodiments, the bacteria is *B. anthracis* (including Ames strain and ciprofloxacin resistant Ames strain) *B. anth*1024, *B. brevis, B. licheniformis, B. megaterium, B. pumilus, B. subtilis, B. vollum*, and spores thereof; *B. cepacia, B. mallei, M. pseudomallei*, and *B. thailandensis; E. coli, E. feacalis, E. faecium*, and vancomycin resistant strains thereof; *K. pneumoniae; P. aeruginosa*, preferably PAO1; *S. aureus* and methicillin resistant *S. aureous; Y. pestis*; or a combination thereof.

The activity of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds a subject suffering from a given disease or disorder. The compounds of the present invention may be used in combination with or as a substitution for treatments known in the art.

The therapeutically effective amounts of the compounds of the invention for treating the diseases or disorders described above in a subject can be determined in a variety of ways known to those of ordinary skill in the art, e.g. by administering various amounts of a particular compound to a subject afflicted with a particular condition and then determining the effect on the subject. Typically, therapeutically effective amounts of a compound of the present invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular subject will depend upon a variety of factors including the activity of the specific compound employed, the age, body weight, general health, sex, diet, time of administration, route of administration, and rate of excretion, drug combination and the severity of the particular disease.

Frequency of dosage may also vary depending on the compound used and the particular disease treated. It will also be appreciated that the effective dosage of the compound used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to bacteria.

As provided herein, an "effective amount" is intended to mean that amount of a compound that is sufficient to reduce, prevent or inhibit BoNT/A LC metalloprotease activity as compared with a negative control. A "therapeutically effective amount" of a compound of the present invention, a prodrug, an active metabolite, or a salt thereof, is a quantity sufficient to, when administered to a subject, reduce, prevent or inhibit BoNT/A LC metalloprotease activity. Also, as used herein, a "therapeutically effective amount" of a compound of the present invention is an amount which prevents, inhibits, suppresses, or reduces a given clinical condition in a subject as compared to a control. As defined herein, a therapeutically effective amount of a compound of the present invention may be readily determined by one of ordinary skill by routine methods known in the art.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), dermal, mucosal, vaginal and parenteral (including subcutaneous, intramuscular, intravenous and intradermal). It will be appreciated that the preferred route will vary with the condition and age of the recipient, the nature of the condition to be treated, and the chosen compound of the present invention.

The compound can be administered alone, but will generally be administered as pharmaceutical formulations suitable for administration. Pharmaceutical formulations known in the art contemplated herein. Pharmaceutical formulations of this invention comprise a therapeutically effective amount of at least one compound of the present invention, and an inert, pharmaceutically or cosmetically acceptable carrier or diluent. As used herein the language "pharmaceutically acceptable carrier" or a "cosmetically acceptable carrier" is intended to include any and all solvents, dispersion media, coatings, antibacterial and antifungal agents, isotonic and absorption delaying agents, and the like, compatible with pharmaceutical or cosmetic administration. Except insofar as any conventional media or agent is incompatible with the active compound, use thereof in the formulation is contemplated. Descriptions of suitable pharmaceutically acceptable carriers, formulations, and factors involved in their selection, are found in a variety of readily available sources, e.g., Remington's Pharmaceutical Sciences, 17$^{th}$ ed., Mack Publishing Company, Easton, Pa., 1985, which is incorporated herein by reference.

Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with bacterial infection and toxic side effects of bacterial infection including intoxication by a toxin. Supplementary active compounds also include those known in the art which delay toxin induced muscle paralysis such as BoNT/A holotoxin induced muscle paralysis.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary active compounds also include other compounds known in the art which inhibit botulinum neurotoxin serotype A light chain metalloprotease activity, anthrax lethal factor protease activity, or a combination thereof such as NSC 240898, NSC 266474, NSC 266476, NSC 290107, NSC 290108, NSC 290109, NSC 294200, NSC 294201, NSC 294203, NSC 294204, NSC 294206, NSC 300511, NSC 308571, NSC 308572, NSC 308574, NSC 317880, NSC 317881, NSC 317884, NSC 317885, 317886, NSC 317887, NSC 341907, NSC 341909, and NSC 341911.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Various compounds of the present invention have been found to exhibit antibacterial activity and prevent the growth and spore germination of bacteria such as *Bacillus, Burkholderia, Enterobacter, Escherichia, Helicobacter, Klebsiella, Mycobacterium, Neisseria, Pseudomonas, Staphylococcus, Streptococcus, Yersinia* and the like, including drug resistance strains. In preferred embodiments, the bacteria is *B. anthracis* (including Ames strain and ciprofloxacin resistant Ames strain) *B. anth*1024, *B. brevis, B. licheniformis, B. megaterium, B. pumilus, B. subtilis, B. vollum*, and spores thereof; *B. cepacia, B. mallei, M. pseudomallei*, and *B. thailandensis; E. coli, E. feacalis, E. faecium*, and vancomycin resistant strains thereof; *K. pneumoniae; P. aeruginosa*, preferably PAO1; *S. aureus* and methicillin resistant *S. aureous; Y. pestis*; or a combination thereof. Various compounds of the present invention, including NSC 240898, NSC 266474, NSC 266476, NSC 290107, NSC 290108, NSC 290109, NSC 294200, NSC 294201, NSC 294203, NSC 294204, NSC 294206, NSC 300511, NSC 308571, NSC 308572, NSC 308574, NSC 317880, NSC 317881, NSC 317884, NSC 317885, 317886, NSC 317887, NSC 341907, NSC 341909, and NSC 341911 are also found to inhibit the protease activity of anthrax lethal factor.

Thus, not only is the present invention directed to methods of inhibiting toxin activity, such as botulinum neurotoxin serotype A light chain metalloprotease activity or the protease activity of anthrax lethal factor, but it is also directed to methods of treating a subject suffering from a bacterial infection.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of inhibiting the activity of Botulinum neurotoxin A metalloprotease which comprises contacting Botulinum neurotoxin A metalloprotease with at least one compound having the following structural formula:

wherein
$X^1$ is S, O or $NR^8$;
$X^2$ is $CR^7$;
L is a linker which may be a direct bond or where Z is an optionally substituted alkyl, alkenyl, dialkenyl, trialkenyl, or aryl; and $R^1$, $R^2$, $R^5$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, aryloxy, aryoxy, cycloalkoxy, heteroaryloxy, alkoxycarbonyl, alkylamino, carbamoyl, alkylaminocarbonyl, alkylsulfhydryl, alkylhydroxymate; and $R^8$ is hydrogen, OH, a halogen, or an optionally substituted alkyl.

2. The method of claim 1, wherein at least one of $R^1$ or $R^2$ is hydrogen, amidine, 2-imidazoline, amino, guanidine, methyl, aminomethyl-hydroxylamine, or methylamine-guanidine.

3. The method of claim 1, wherein $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine.

4. The method of claim 1, wherein $CR^7$ is CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

5. The method of claim 1, wherein at least one of $R^1$, $R^2$, $R^5$ or $R^7$ is —H, —$CH_3$, —$NH_2$,

6. The method of claim 1, wherein $R^5$ is —$NH_2$,

[structures shown]

7. The method of claim 1, wherein $R^7$ is —H, —$CH_3$, —$NH_2$,

[structures shown]

8. The method of claim 1, wherein $R^8$ is —H, —$(CH_2)_2OH$, or —$(CH_2)_2Cl$.

9. The method of claim 1, wherein L is a direct bond,

[structures shown]

[-continued structure shown]

10. The method of claim 1, wherein the compound has the following structural formula:

[structure with $R^1$, $R^2$, $X^1$, $X^2$, L, $R^5$]

11. A method of inhibiting the activity of Botulinum neurotoxin A metalloprotease which comprises contacting Botulinum neurotoxin A metalloprotease with at least one compound selected from the group consisting of NSC 92833, NSC 103699, NSC 103701, NSC 130681, NSC 240890, NSC 240891, NSC 240893, NSC 240894, NSC 240895, NSC 240896, NSC 240897, NSC 240898, NSC 240899, NSC 240900, NSC 266472, NSC 266474, NSC 266475, NSC 266476, NSC 266477, NSC 266482, NSC 278995, NSC 278996, NSC 278997, NSC 278999, NSC 290107, NSC 290108, NSC 290109, NSC 290111, NSC 291103, NSC 294199, NSC 294200, NSC 294201, NSC 294202, NSC 294203, NSC 294204, NSC 294206, NSC 294207, NSC 294208, NSC 294494, NSC 300509, NSC 300510, NSC 300511, NSC 300512, NSC 302569, NSC 308569, NSC 308570, NSC 308571, NSC 308572, NSC 308573, NSC 308574, NSC 317880, NSC 317881, NSC 317883, NSC 317884, NSC 317885, NSC 317886, NSC 317887, NSC 328398, NSC 330687, NSC 330688, NSC 330689, NSC 330690, NSC 341082, NSC 341907, NSC 341909, NSC 341910, NSC 341911, NSC 352341, NSC 369718, NSC 369721, NSC 607617, and NSC 12155.

12. The method of claim 11, wherein the compound is NSC 341909, NSC 308574, NSC 240898, NSC 341907, NSC 266472, NSC 330690, NSC 278999, NSC 308571, NSC 290107, NSC 290108, NSC 294200, NSC 317884, NSC 317884, NSC 294203, NSC 294494, NSC 317881, NSC 330688, NSC 317886, NSC 317833, NSC 328398 NSC 352341, NSC 294204, NSC 341911, NSC 300511, NSC 607617, NSC 294202, NSC 317880, NSC 240899, NSC 294201, NSC 291103, NSC 308573, NSC 290109, NSC 294206, NSC 308570, NSC 294199, NSC 369723, or NSC 300510.

13. The method of claim 1, wherein the compound has the following structural formula:

[structure shown]

-continued
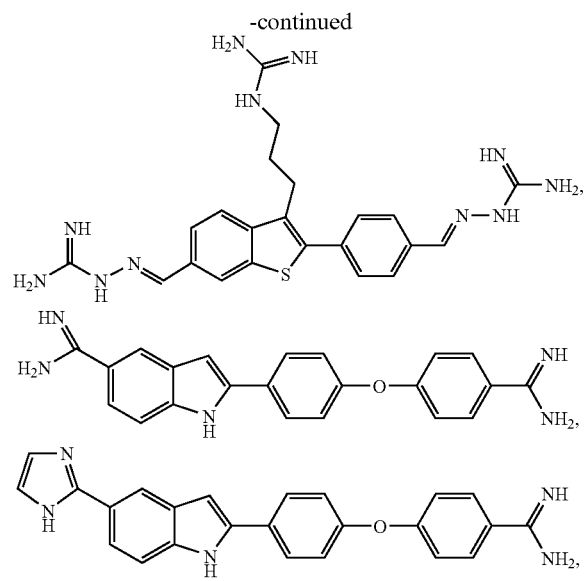
-continued
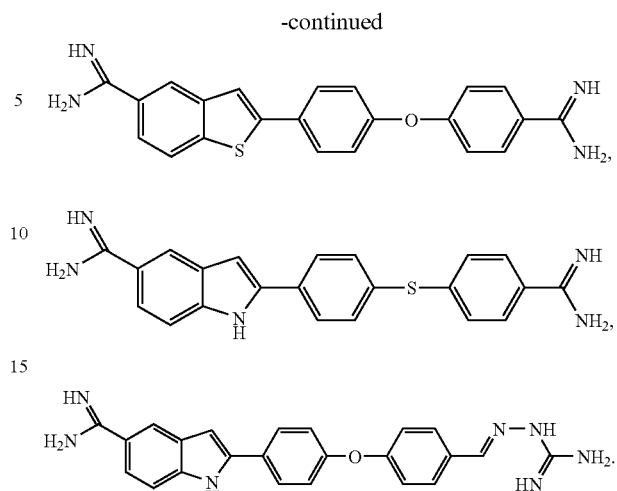
* * * * *